United States Patent
Wold et al.

(10) Patent No.: US 6,811,977 B2
(45) Date of Patent: Nov. 2, 2004

(54) RAPID, QUANTITATIVE METHOD FOR THE MASS SPECTROMETRIC ANALYSIS OF NUCLEIC ACIDS FOR GENE EXPRESSION AND GENOTYPING

(75) Inventors: Barbara J. Wold, Pasadena, CA (US); John F. Murphy, Pasadena, CA (US); Mark E. Davis, Pasadena, CA (US); Kent Kirshenbaum, Pasadena, CA (US); David A. Tirrell, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 107 days.

(21) Appl. No.: 09/918,687

(22) Filed: Jul. 27, 2001

(65) Prior Publication Data

US 2002/0137057 A1 Sep. 26, 2002

Related U.S. Application Data

(60) Provisional application No. 60/221,479, filed on Jul. 27, 2000.

(51) Int. Cl.[7] .............................. C12Q 1/68; C12P 19/34
(52) U.S. Cl. ............................ 435/6; 435/91.2; 436/94; 436/173; 530/350; 250/282
(58) Field of Search ...................... 435/6, 91.2; 436/94, 436/173; 250/282

(56) References Cited

U.S. PATENT DOCUMENTS

| | | | |
|---|---|---|---|
| 5,112,739 A | 5/1992 | Meneghini et al. | |
| 5,681,943 A | 10/1997 | Letsinger et al. | |
| 5,695,937 A | * 12/1997 | Kinsler et al. | 435/6 |
| 5,811,387 A | 9/1998 | Simon et al. | |
| 5,952,202 A | 9/1999 | Aoyagi et al. | 435/91.2 |
| 6,043,031 A | * 3/2000 | Koster et al. | 435/6 |
| 6,635,452 B1 | * 10/2003 | Monforte et al. | 435/91.1 |

* cited by examiner

*Primary Examiner*—Jeffrey Fredman
(74) *Attorney, Agent, or Firm*—Gray Cary Ware & Freidenrich, LLP

(57) ABSTRACT

The invention provides methods of identifying one or more nucleic acids in a sample. The nucleic acids, for example, expressed genes in a cell, can be identified by contacting the nucleic acids with oligonucleotides having detector tags, and selector tags to form tagged oligonucleotides. Each nucleic acid can be uniquely identified by mass-spectrophotometric analysis of the detector tag.

33 Claims, 25 Drawing Sheets

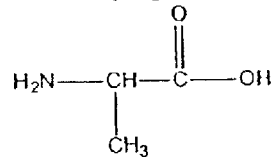
alanine (Peptide monomer)
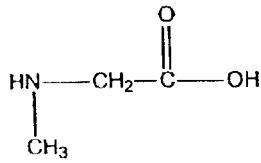
Sarcosine (Peptoid monomer)
vs.
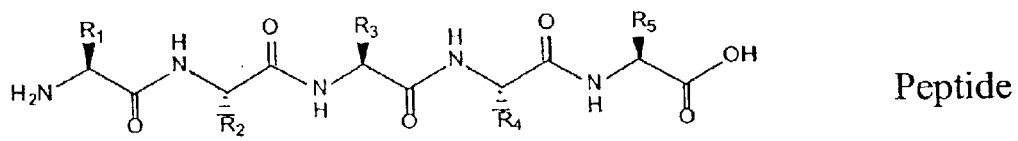
Peptide
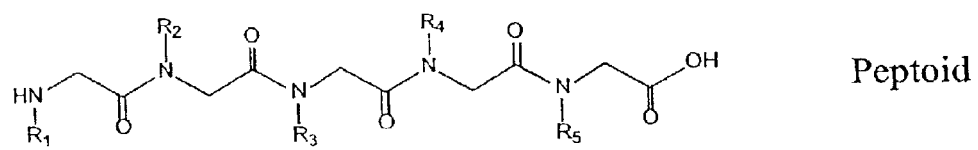
Peptoid
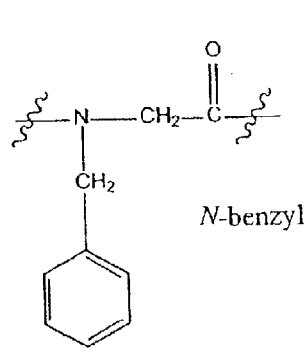
N-benzyl
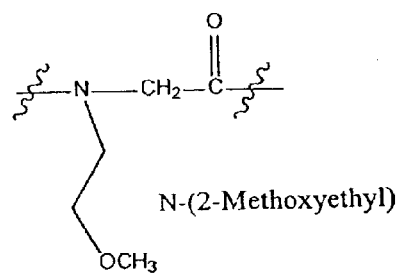
N-(2-Methoxyethyl)
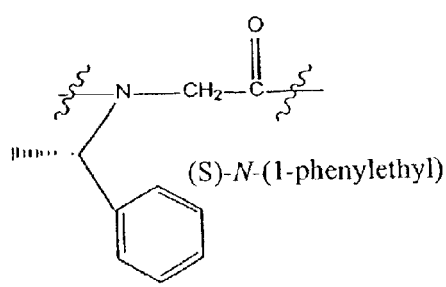
(S)-N-(1-phenylethyl)
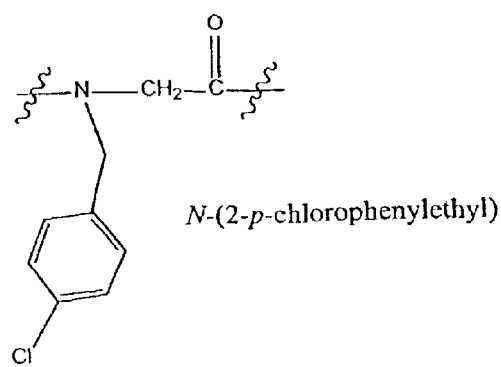
N-(2-p-chlorophenylethyl)
FIGURE 4

| M\N | 13 | 14 | 15 | 16 | 17 | 18 | 19 | 20 | 21 | 22 | 23 | 24 | 25 |
|---|---|---|---|---|---|---|---|---|---|---|---|---|---|
| | 11 | 12 | 13 | 1 | 14 | 15 | 16 | 17 | 1 | 18 | 19 | 20 | 21 |
| 1 | 104 | 119 | 135 | 152 | 170 | 189 | 209 | 230 | 252 | 275 | 299 | 324 | 350 |
| 2 | 559 | 679 | 815 | 968 | 1139 | 1329 | 1539 | 1770 | 2023 | 2299 | 2599 | 2924 | 3275 |
| 3 | 2379 | 3059 | 3875 | 4844 | 5984 | 7314 | 8854 | 10625 | 12649 | 14949 | 17549 | 20474 | 23750 |
| 4 | 8567 | 11627 | 15503 | 20348 | 26333 | 33648 | 42503 | 53129 | 65779 | 80729 | 98279 | 118754 | 142505 |
| 5 | 27131 | 38759 | 54263 | 74612 | 100946 | 134595 | 177099 | 230229 | 296009 | 376739 | 475019 | 593774 | 736280 |
| 6 | 77519 | 116279 | 170543 | 245156 | 346103 | 480699 | 657799 | 888029 | 1184039 | 1560779 | 2035799 | 2629574 | 3355855 |
| 7 | 203489 | 319769 | 490113 | 735470 | 1081574 | 1562274 | 2220074 | 3108104 | 4292144 | 5852924 | 7888724 | 10516299 | 13884155 |
| 8 | 497419 | 817189 | 1307503 | 2042974 | 3124549 | 4688824 | 6906399 | 10015004 | 14307149 | 20160074 | 28046799 | 38567099 | 52451255 |
| 9 | 1144065 | 1931255 | 3266759 | 5311734 | 8436284 | 13123109 | 20030009 | 30045014 | 44352164 | 64512239 | 92561039 | 131128139 | 183579335 |
| 10 | 2496143 | 4457399 | 7726159 | 13037894 | 21474179 | 34597289 | 54627299 | 84672314 | 129024479 | 193536719 | 285097759 | 417225899 | 600306295 |
| 11 | 5200299 | 9657659 | 17363859 | 30421754 | 51895934 | 86493224 | 141120524 | 225792839 | 354817319 | 548354039 | 834451799 | 1251677699 | 1852482995 |
| 12 | 10400599 | 20058299 | 37442159 | 67863914 | 119759849 | 206253074 | 347373599 | 573166439 | 927983759 | 1476337799 | 2310785599 | 3562467299 | 5414950295 |
| 13 | 20058299 | 40115599 | 77558759 | 145422674 | 265182524 | 471435599 | 818809199 | 1391975639 | 2319959399 | 3796297199 | 6107086799 | 9669554099 | 15084504395 |
| 14 | 37442159 | 77558759 | 155175199 | 300540194 | 565722719 | 1037158319 | 1855967519 | 3247943159 | 5567902559 | 9364199759 | 15471286559 | 25140840659 | 40225345055 |
| 15 | 67863914 | 145422674 | 300540194 | 601080389 | 1166803109 | 2203961429 | 4059928949 | 7307872109 | 12875774669 | 22239974429 | 37711260989 | 62852101649 | |
| 16 | 119759849 | 265182524 | 565722719 | 1166803109 | 2333605219 | 4537567649 | 8597496599 | 15905368709 | 28781143379 | 51021117809 | 88732378799 | 1.51584E+11 | 2.54662E+11 |
| 17 | 206253074 | 471435599 | 1037158319 | 2203961429 | 4537567649 | 9075135299 | 17672631899 | 33578000609 | 62359143989 | 1.1338E+11 | 2.02113E+11 | 3.53697E+11 | 6.08359E+11 |
| 18 | 347373599 | 818809199 | 1855967519 | 4059928949 | 8597496599 | 17672631899 | 35345263799 | 68923264409 | 1.31282E+11 | 2.44663E+11 | 4.46775E+11 | 8.00472E+11 | 1.40883E+12 |
| 19 | 573166439 | 1391975639 | 3247943159 | 7307872109 | 15905368709 | 33578000609 | 68923264409 | 1.37847E+11 | 2.69129E+11 | 5.13792E+11 | 9.60567E+11 | 1.76104E+12 | 3.16987E+12 |
| 20 | 927983759 | 2319959399 | 5567902559 | 12875774669 | 28781143379 | 62359143989 | 1.31282E+11 | 2.69129E+11 | 5.38258E+11 | 1.05205E+12 | 2.01262E+12 | 3.77366E+12 | 6.94353E+12 |
| 21 | 1476337799 | 3796297199 | 9364199759 | 22239974429 | 51021117809 | 1.1338E+11 | 2.44663E+11 | 5.13792E+11 | 1.05205E+12 | 2.1041E+12 | 4.11672E+12 | 7.89037E+12 | 1.48339E+13 |
| 22 | 2310789599 | 6107086799 | 15471286559 | 37711260989 | 88732378799 | 2.02113E+11 | 4.46775E+11 | 9.60567E+11 | 2.01262E+12 | 4.11672E+12 | 8.23343E+12 | 1.61238E+13 | 3.09577E+13 |
| 23 | 3562467299 | 9669554099 | 25140840659 | 62852101649 | 1.51584E+11 | 3.53697E+11 | 8.00472E+11 | 1.76104E+12 | 3.77366E+12 | 7.89037E+12 | 1.61238E+13 | 3.22476E+13 | 6.32053E+13 |
| 24 | 5414950295 | 15084504395 | 40225345055 | 1.03077E+11 | 2.54662E+11 | 6.08359E+11 | 1.40883E+12 | 3.16987E+12 | 6.94353E+12 | 1.48339E+13 | 3.09577E+13 | 6.32053E+13 | 1.25411E+14 |
| 25 | 8122425443 | 23206929839 | 63432274895 | 1.6651E+11 | 4.21172E+11 | 1.02953E+12 | 2.43835E+12 | 5.60823E+12 | 1.25518E+13 | 2.73857E+13 | 5.83434E+13 | 1.21549E+14 | 2.47959E+14 |
| 26 | 12033222879 | 35240152719 | 98672427615 | 2.65182E+11 | 6.86354E+11 | 1.71588E+12 | 4.15425E+12 | 9.76248E+12 | 2.23142E+13 | 4.99999E+13 | 1.08043E+14 | 2.25592E+14 | 4.77551E+14 |
| 27 | 17620076359 | 52260229079 | 1.51535E+11 | 4.16715E+11 | 1.10307E+12 | 2.81895E+12 | 6.9732E+12 | 1.67357E+13 | 3.90499E+13 | 8.87498E+13 | 1.96793E+14 | 4.26385E+14 | 9.03936E+14 |
| 28 | 25518731279 | 78378960359 | 2.29912E+11 | 6.46626E+11 | 1.7497E+12 | 4.56865E+12 | 1.15418E+13 | 2.82775E+13 | 6.73274E+13 | 1.56077E+14 | 3.5287E+14 | 7.79255E+14 | 1.68319E+15 |
| 29 | 36576848167 | 1.14956E+11 | 3.44867E+11 | 9.91484E+11 | 2.74119E+12 | 7.30984E+12 | 1.88517E+13 | 4.71292E+13 | 1.14457E+14 | 2.70534E+14 | 6.23404E+14 | 1.40266E+15 | 3.08585E+15 |
| 30 | 51915526431 | 1.66871E+11 | 5.11739E+11 | 1.50323E+12 | 4.24442E+12 | 1.15543E+13 | 3.04059E+13 | 7.75352E+13 | 1.91992E+14 | 4.62526E+14 | 1.08593E+15 | 2.48859E+15 | 5.57444E+15 |
| 31 | 73006209044 | 2.39878E+11 | 7.51610E+11 | 2.25485E+12 | 6.49927E+12 | 1.80535E+13 | 4.84595E+13 | 1.25995E+14 | 3.17986E+14 | 7.85512E+14 | 1.86644E+15 | 4.35503E+15 | 9.92947E+15 |
| 32 | 1.01766E+11 | 3.41644E+11 | 1.09326E+12 | 3.34811E+12 | 9.84738E+12 | 2.79009E+13 | 7.63604E+13 | 2.02355E+14 | 5.20341E+14 | 1.30085E+15 | 3.16735E+15 | 7.52233E+15 | 1.74518E+16 |
| 33 | 1.40677E+11 | 4.82321E+11 | 1.57586E+12 | 4.92906E+12 | 1.47711E+13 | 4.26725E+13 | 1.19032E+14 | 3.21387E+14 | 8.41729E+14 | 2.14256E+15 | 5.30988E+15 | 1.28322E+16 | 3.0284E+16 |
| 34 | 1.92928E+11 | 6.75249E+11 | 2.25083E+12 | 7.17452E+12 | 2.19456E+13 | 6.46176E+13 | 1.8365E+14 | 5.05037E+14 | 1.34677E+15 | 3.48935E+15 | 8.79923E+15 | 2.16314E+16 | 5.19154E+16 |
| 35 | 2.62597E+11 | 9.37846E+11 | 3.18968E+12 | 1.03632E+13 | 3.23068E+13 | 9.69263E+13 | 2.80676E+14 | 7.85614E+14 | 2.13238E+15 | 5.62173E+15 | 1.4421E+16 | 3.60524E+16 | 8.79678E+16 |
| 36 | 3.54861E+11 | 1.29271E+12 | 4.48138E+12 | 1.48446E+13 | 4.71534E+13 | 1.4408E+14 | 4.24656E+14 | 1.21027E+15 | 3.34265E+15 | 8.96438E+15 | 2.33853E+16 | 5.94377E+16 | 1.47406E+17 |
| 37 | 4.7626E+11 | 1.76897E+12 | 6.25035E+12 | 2.10949E+13 | 6.82483E+13 | 2.12328E+14 | 6.36984E+14 | 1.84725E+15 | 5.1899E+15 | 1.41543E+16 | 3.75396E+16 | 9.69773E+16 | 2.44835E+17 |
| 38 | 6.35014E+11 | 2.40398E+12 | 8.65433E+12 | 2.97493E+13 | 9.79975E+13 | 3.10326E+14 | 9.47309E+14 | 2.79456E+15 | 7.98447E+15 | 2.21387E+16 | 5.96784E+16 | 1.56656E+17 | 4.01039E+17 |
| 39 | 8.41393E+11 | 3.24537E+12 | 1.18997E+13 | 4.1649E+13 | 1.39646E+14 | 4.49972E+14 | 1.39728E+15 | 4.19184E+15 | 1.21763E+16 | 3.43151E+16 | 9.39934E+16 | 2.50649E+17 | 6.51688E+17 |
| 40 | | | | | | | | | | | | | |

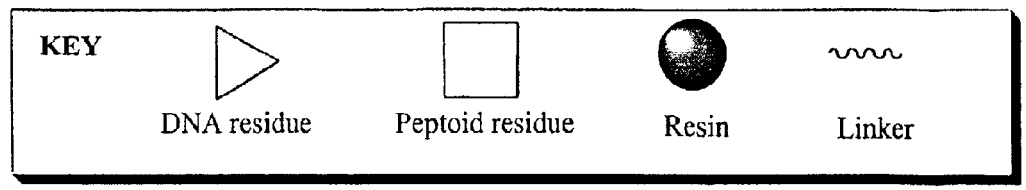
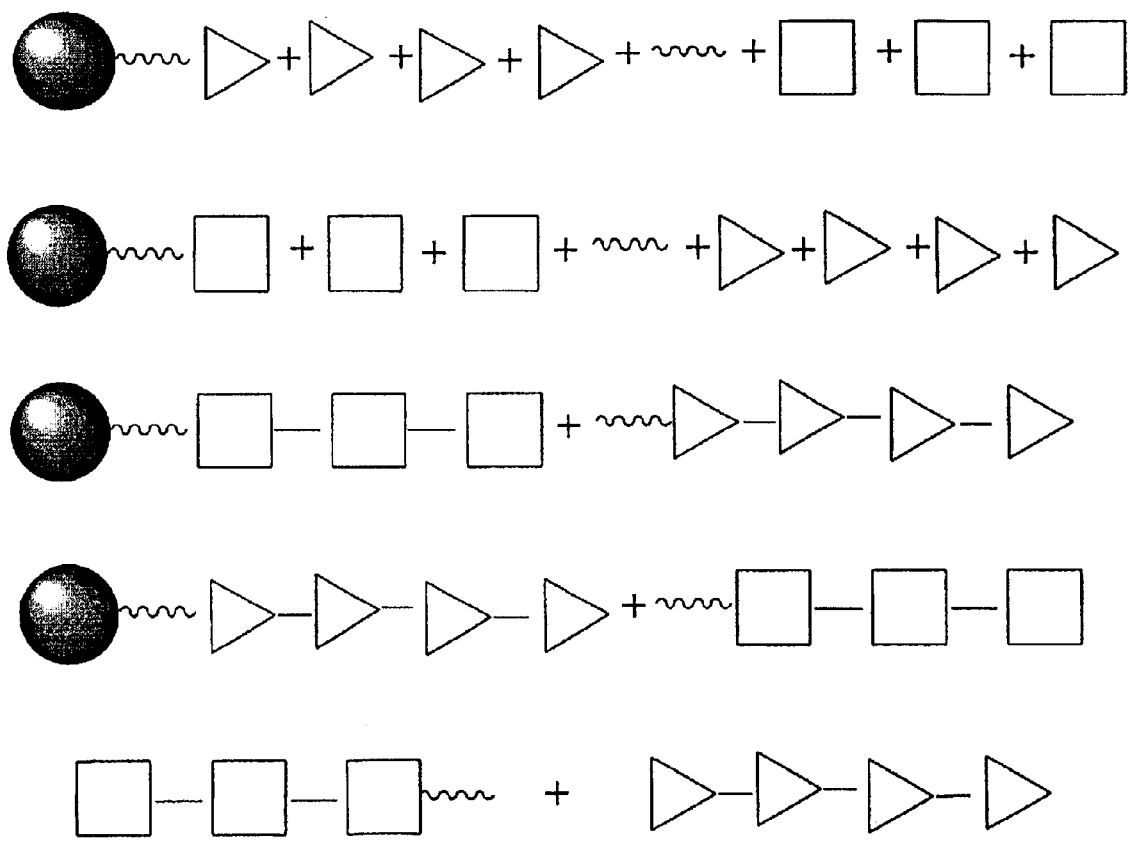
FIGURE 9

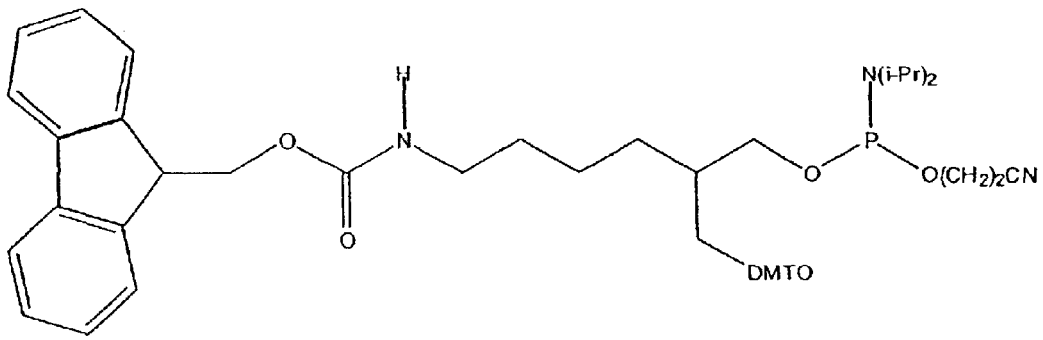

Clontech "Uni-Link AminoModifier" Branched Phosphoramidite

Method

1. Obtain Oligonucleotide Resin with dT base    ●—dT

2. Add Branched Phosphoramidite

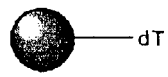

3. Transfer to Peptoid Synthesizer

4. Deprotect FMOC

5. Add Peptoid

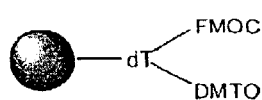

6. Protect Terminus

7. Return to ODN Synthesizer

8. Deprotect DMTO

9. Add cleavable units (Disulfide or Photocleavable)

10. Synthesize ODN

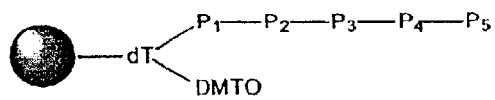

11. Deprotect and Cleave Completed Unit

FIGURE 12

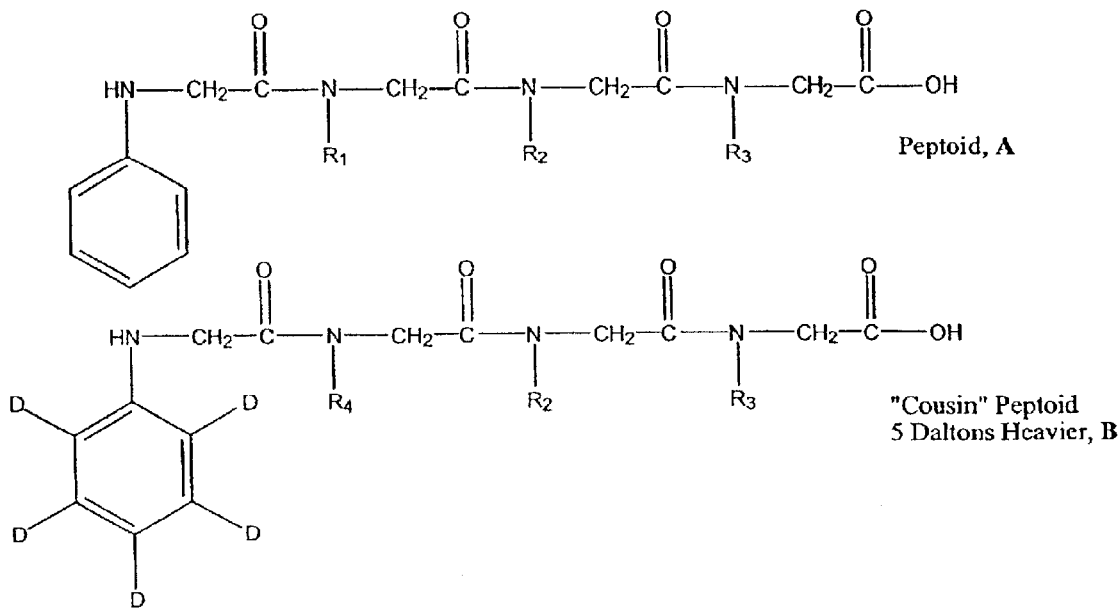
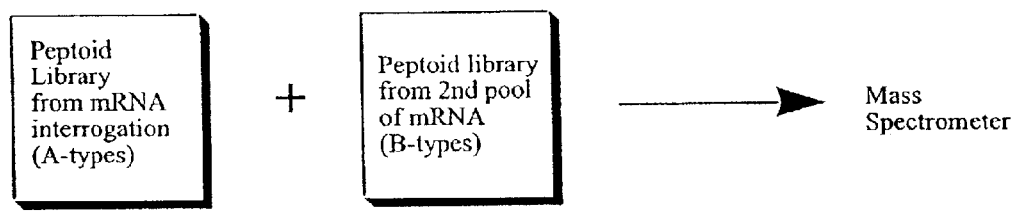
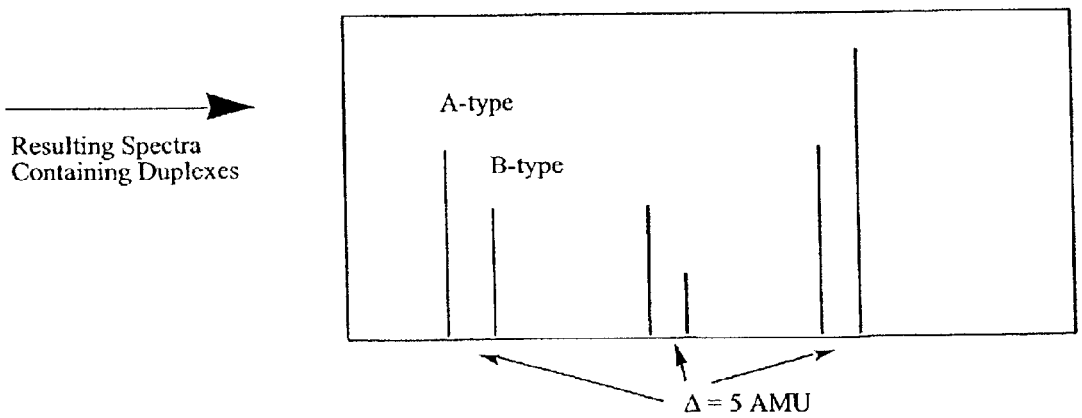
FIGURE 17

1) Synthesize and purify 1000 different peptoid oligomer mass tags, of mass 6,000 to 11,000 Daltons.

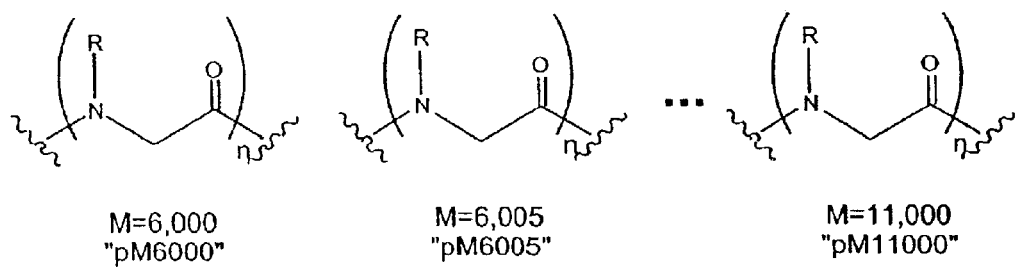

M=6,000　　　　　M=6,005　　　　　M=11,000
"pM6000"　　　　"pM6005"　　　　"pM11000"

This will be performed by a robotic synthesizer on solid phase, with oligomer lengths of up to 40 residues. Molecular weights per residue will be 150-300 Daltons.

2) Synthesize and purify 16,000 different DNA oligos, complementary to the mRNA specie to be detected. Create 16 libraries of 1,000 oligos each.

$AA(NNNNNNNN)_1$, $AA(NNNNNNNN)_2$, ...., $AA(NNNNNNNN)_{1,000}$ $AC(NNNNNNNN)_1$, $AC(NNNNNNNN)_2$, ...., $AC(NNNNNNNN)_{1,000}$

.................................................................................................

$TT(NNNNNNNN)_1$, $TT(NNNNNNNN)_2$, ...., $TT(NNNNNNNN)_{1,000}$

3) Specifically conjugate oligos in each library to a corresponding peptoid mass tag.

$AA(NNNNNNNN)_1/pM6000$, $AA(NNNNNNNN)_2/pM6005$, ...., $AA(NNNNNNNN)_{1,000}/pM11000$ $AC(NNNNNNNN)_1/pM6000$, $AC(NNNNNNNN)_2/pM6005$, ...., $AC(NNNNNNNN)_{1,000}/pM11000$

.................................................................................................

$TT(NNNNNNNN)_1/pM6000$, $TT(NNNNNNNN)_2/pM6005$, ...., $TT(NNNNNNNN)_{1,000}/pM11000$

4) Purify DNA/peptoid mass tag products and combine library elements into 16 pools.

FIGURE 19

RAPID, QUANTITATIVE METHOD FOR THE MASS SPECTROMETRIC ANALYSIS OF NUCLEIC ACIDS FOR GENE EXPRESSION AND GENOTYPING

RELATED APPLICATIONS

This application claims the benefit of priority under 35 U.S.C. §119(e) to United States Provisional Application 60/221,479, filed Jul. 27, 2000, the entire contents of which is incorporated herein by reference.

FIELD OF THE INVENTION

The invention relates generally to methods for detecting and measuring the level of nucleic acids, and specifically to detection and measurement methods using mass spectrometry.

BACKGROUND

Although a variety of methods to detect and measure nucleic acids have been developed, no method provides a highly accurate means of detecting many genes in a biological sample. The simplest method in common practice for detection of mRNA transcripts is the northern blot. Northern blot analysis can be used to detect a small number of transcripts of interest, however quantitation of the level of a specific transcript using northern blot analysis is difficult and often inaccurate. RT-PCR can be used on its own or in an intermediate-scale method known as the rapid analysis of gene expression (RAGE). RT-PCR and RAGE suffer from biases resulting from the PCR priming and amplification process and are further limited by the use of measurement of band intensity on gels to quantify gene levels. In addition, the methods are not well-suited to a high level multiplexing, i.e., measuring many genes at once in a single sample.

In order to address the poor quantitation of previous methods, newer methods based on sequencing have been suggested. One such method, serial analysis of gene expression (SAGE), allows the quantitative and simultaneous analysis of a large number of transcripts. In SAGE, the cDNA library constructed from all the transcripts in a cell, i.e., the transcriptome, is concatenated into large chunks and then sequenced. The sequencing data is computationally converted into quantitative levels of gene expression via the frequency of occurrence of sequences representing a given gene transcript. This method can also be used for gene discovery, but it cannot be targeted to specific subsets of genes of interest (e.g., all known oncogenes or all known tumor suppressors or all known G-coupled membrane receptors). SAGE is accurate, but it is slow and relatively expensive since it requires a large amount of sequencing for each sample to be studied.

One new method, called massively parallel signature sequencing (MPSS), is a high throughput method making use of specially litigated adapters and signature sequencing. It is sequencing-based and suffers many of the same disadvantages as SAGE, but it is more efficient because separation of cDNA fragments is not required.

The most common methods in practice for large-scale analysis of the transcriptome employ DNA microarrays, either robotically spotted or microfabricated. Such arrays permit biologists to monitor 5–10,000 genes per experiment in most implementations, for example, by using a DNA chip, provided that the experiment begins with large amounts of starting sample. Thus, RNA extraction must be from sizable amounts of tissue, cell or embryo cultures, or that the initial RNA sample must be amplified via various PCR-based strategies. It would be highly desirable to eliminate amplification steps and to instead make measurements of RNA presence and levels directly.

Methods using microarrays suffer various limitations. First, microarrays rely on hybridization to cDNAs or oligonucleotides that are bound to the surface of a solid support. The kinetics and physics of such interactions are poorly understood and difficult to optimize in comparison to hybridization interactions in liquid phase. For example, inconsistencies can be introduced during the creation of DNA samples that are deposited or synthesized on the solid matrix. Furthermore, diffusion parameters and the limited accessibility of DNA fixed onto the chip to test samples all conspire to make quantitation and reproducibility difficult. Second, microarrays require a relatively large amount of input RNA to achieve high sensitivity, particularly when rare genes are assessed. Third, microarrays have a limited dynamic range. Cells express RNA significantly over four or five orders of magnitude, and microarrays are only capable of working within one or two orders of magnitude. These issues of input material severely constrain their applications in biology where the investigator wants to assay the transcriptome in small groups of cells or individual cells. This arises often in developmental biology, neurobiology and increasingly in other biological fields. Arrays typically require material from $10^6$ cells or more per 10,000 genes measured. Fourth, microarrays are technically difficult to fabricate, and have a high per-experiment cost. Finally, quantitatively accuracy is limited since microarrays meant to deliver identical results differ by greater than 200%, which is greater than biologically significant differences in gene expression. Sensitive computer algorithms used to evaluate microarray data do not rectify this problem since they perform poorly with high or variable noise levels in the data.

There is thus a need for a highly sensitive method for detecting nucleic acids in biological samples. The present invention meets that need and more.

SUMMARY OF THE INVENTION

In one embodiment, the invention provides a method of detecting a specific nucleic acid in a sample. The method includes contacting the nucleic acid with a first oligonucleotide linked to a selector tag and a second oligonucleotide linked to a detector tag, in a reaction mixture under conditions that allow the first and second oligonucleotides to specifically hybridize with the nucleic acid. The first and second oligonucleotides hybridized in such a way that the first oligonucleotide is located immediately adjacent to the second oligonucleotide to form adjacently hybridized first and second oligonucleotides. Next, the adjacently hybridized first and second oligonucleotides are ligated to form a ligated oligonucleotide, and the detector tag associated with the ligated oligonucleotide is identified.

Another embodiment of the invention provides a method of detecting a plurality of specific nucleic acids in a sample. The method includes contacting each specific nucleic acid with an oligonucleotide pair in a reaction mixture under conditions that allow the oligonucleotide pair to specifically hybridize to the nucleic acid such that the oligonucleotide pair members are located immediately adjacent to each other thereby forming an adjacently hybridized oligonucleotide pair. Each oligonucleotide pair comprises a first oligonucleotide linked to a selector tag and a second oligonucleotide linked to a detector tag. Each adjacently hybridized oligonucleotide pair is ligated to form one or more ligated oligonucleotides; and the one or more detector tags associated with the one or more ligated oligonucleotides is identified.

Still another embodiment of the invention provides a method of detecting a nucleic acid in a sample. The method includes amplifying the nucleic acid with a primer pair to form a dual-tagged amplification product in a reaction mixture. The primer pair is a first oligonucleotide linked to a selector tag and a second oligonucleotide linked to a detector tag. Following amplification, the detector tag associated with the dual-tagged amplification product is identified.

Yet another embodiment of the invention provides a method of detecting a nucleic acid in a sample. The method includes contacting the nucleic acid with an oligonucleotide linked to a detector tag under conditions that allow the oligonucleotide to specifically hybridize to the nucleic acid to form a mixture of hybridized oligonucleotide and unhybridized oligonucleotide. A next step includes separating the hybridized oligonucleotide from the unhybridized oligonucleotide; and identifying the detector tag, thereby detecting the nucleic acid.

Another embodiment of the invention provides a kit containing an oligonucleotide primer pair and an agent that binds to the selector tag. The primer pair includes a first selector oligonucleotide linked to a selector tag and a second selector oligonucleotide linked to a detector tag.

Still another embodiment of the invention provides a kit containing a first selector oligonucleotide linked to a selector tag, a second selector oligonucleotide linked to a detector tag, and a DNA ligase.

Another embodiment of the invention provides libraries of oligonucleotides. The oligonucleotides can be linked to detector tags and selector tags.

BRIEF DESCRIPTION OF THE FIGURES

FIG. 4 shows peptoids or N-substituted glycines and their relationship to peptides. Oligomers of length two to approximately forty residues can be formed. The four structures at the bottom of the figure are exemplary peptoid residues.

FIG. 7 shows the number of possible peptoids of unique mass, L, barring coincidences of different structure yet identical mass. M=length of polypeptoid and N=number of monomers of unique mass.

FIG. 9 shows a variety of strategies for linking the oligomeric mass tag to the oligomeric deoxyribonucleic acid. Both are grown on solid supports using a variety of possible growth chemistries. Some of these have the advantage of being "one-pot," others allow pre-purification, and others prevent certain undesirable chemical incompatibilities.

FIG. 12 shows the method of peptoid-oligonucleotide conjugate synthesis using the branched phosphoramidite. This method protects the ODN and the linker from peptoid synthesis chemistry.

FIG. 17 shows a strategy =in which the B-type tags were used as detectors for a second library of mRNA. Thus the relative abundance of each would express the relative differences in gene expression between those two cell types.

FIG. 19 shows an example of the use of peptoid mass tags on a very large scale with applications for the microfabricated scheme.

DETAILED DESCRIPTION OF THE INVENTION

Figure 1:
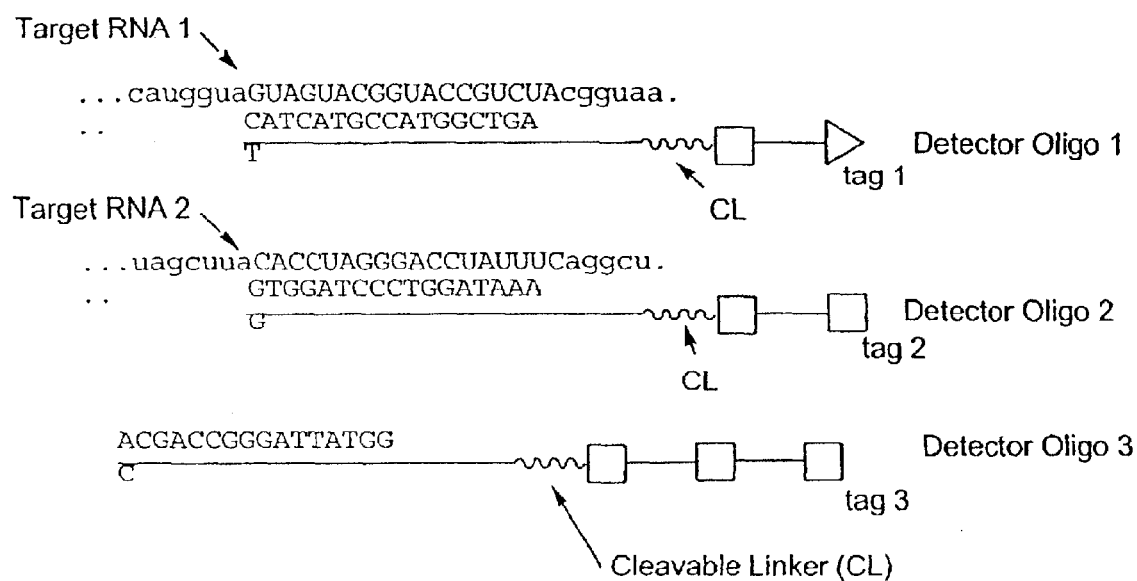
FIG. 1 shows the design of three different detector oligonucleotides (SEQ ID NO:1, SEQ ID NO:3, and SEQ ID NO:5) shown annealed with two corresponding target RNAs (SEQ ID NO:2 and SEQ ID NO:4). In use, the linker (CL) joining the oligonucleotide to the detector tag would be cleaved after those oligonucleotides that have hybridized with target RNA (or DNA) are separated from detector oligonucleotides that have not annealed (e.g., tag 3). The liberated tags (1 and 2) would then be mixed with isotopic internal standards and detected by MS. The squares and triangles, in the peptoid implementation, represent peptoid monomers of different molecular weights, combined in a library having a known distribution.
Figure 2:
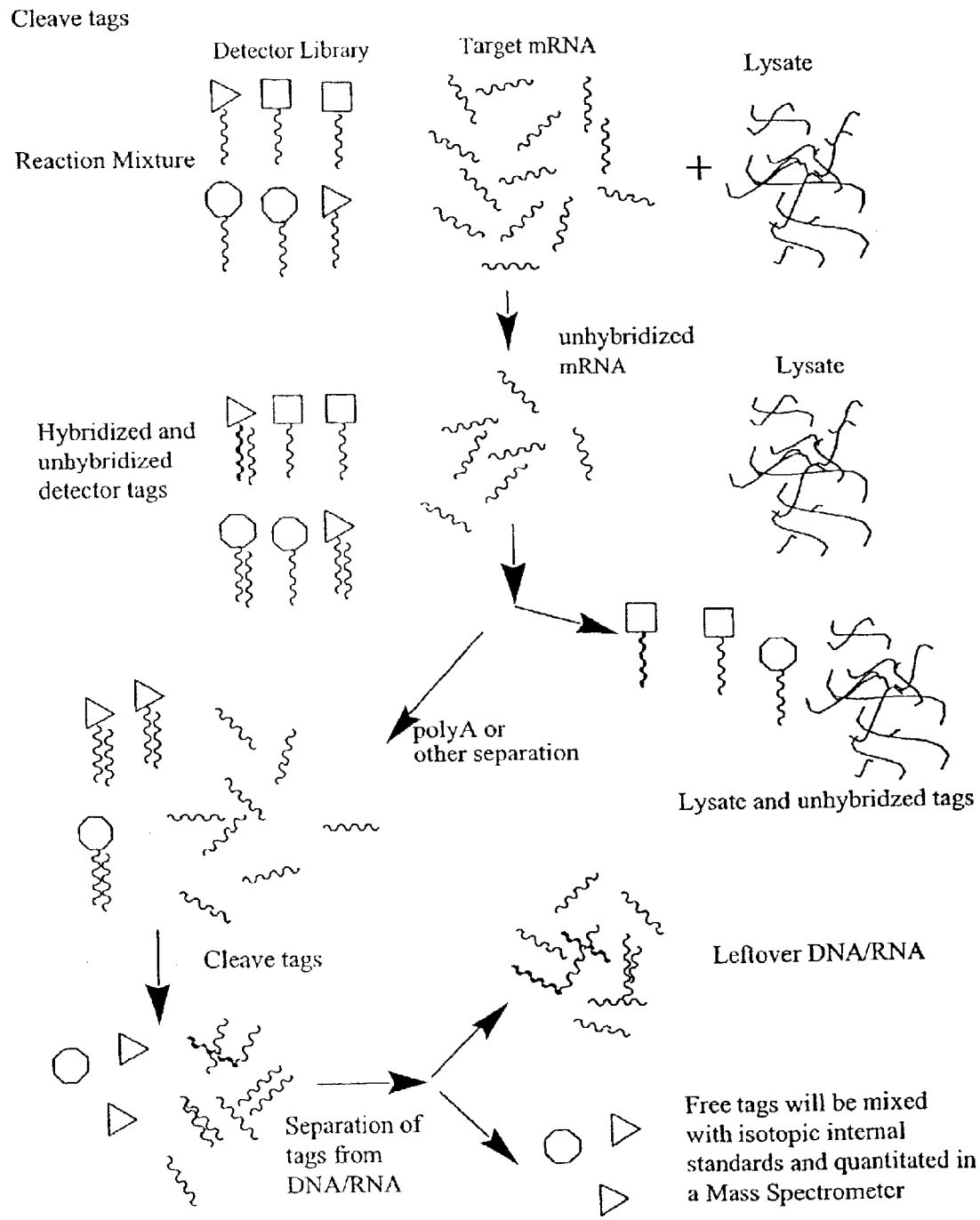
FIG. 2 shows the schematic for use of mass tagged detector oligonucleotides. Detector oligonucleotides are as shown in FIG. 1. An alternative separation scheme would first remove all single stranded DNA, thus removing unhybridized material before the poly A or other enrichment for hybridized material.
Figure 3:
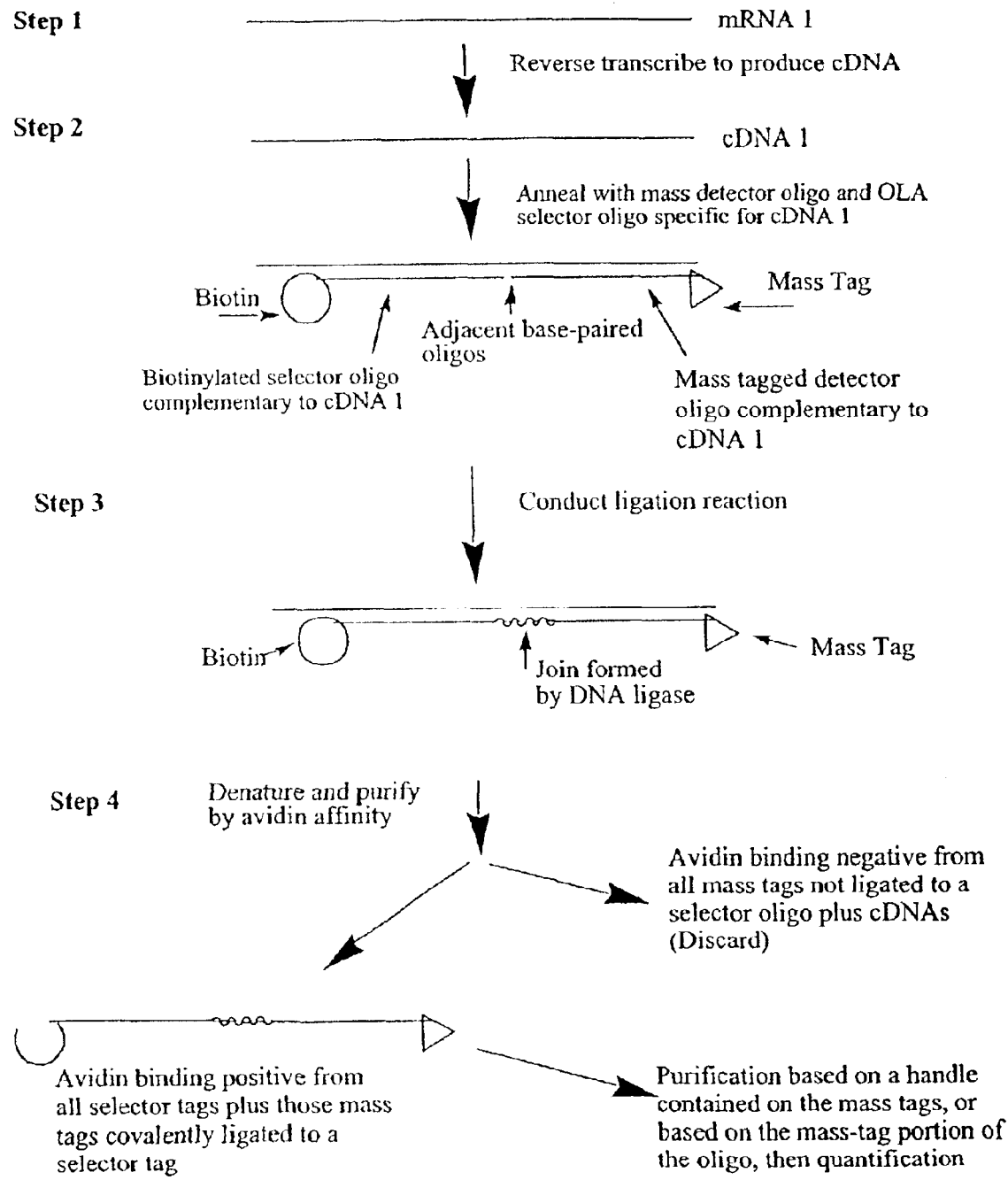
FIG. 3 shows the use of selector oligonucleotides and ligation to increase specificity of mass tagged expression detection and to improve signal to noise ratios. Example uses standard oligonucleotide ligation and biotin/avidin separation.

The present invention provides a method to detect and quantitate one or more specific nucleic acids in a sample.

expressed in low abundance. The method has a dynamic range at least as large as that of the transcriptome itself. MAGE can be performed on a minimum amount of material, as little as a single cell, resulting in reliable quantification. MAGE also provides a method for simultaneously measuring nucleic acid abundance more easily than two at a time (i.e., greater-than-two-color assay). Furthermore, invention methods can be practiced with starting material from total RNA or merely cell lysate, instead of purified mRNA.

MAGE would provide data with great robustness and well understood error sources, so that the data would have the maximum amount of utility in the variety of data mining techniques that are being developed. This tool would also eliminate the need for reliance on housekeeping genes as standards, and it would be capable of providing transcript counts like SAGE, but without the expense or difficulty of sequencing. The assay should be simple to operate, based on well-understood physics, and be as rapid and low-cost as possible.

The invention provides a method of detecting a specific nucleic acid in a sample. Specific nucleic acids are typically messenger RNA (mRNA) or cDNA and therefore code for a gene of interest. In addition specific nucleic acids of other types, i.e., hnRNA, rRNA, tRNA, snRNAs, and the like are also detectable by invention methods. RNA can be obtained from any organism and collected from a single cell, group of cells, tissues or organs. The transcriptome contains a wide variety of mRNA species. The majority of genes in the genome are expressed in very small quantities (Table 1). Furthermore, most of the very tightly regulated genes, which are of great interest, are in this scarce category. The total number of mRNA molecules in each class can be estimated by multiplying the estimated copies per cell of each mRNA sequence by the number of different mRNA sequences each class. Each specific nucleic acid contains at least one known sequence that serves as a target sequence.

|  | Copies per Cell of Each mRNA sequence | | Number of Different mRNA Sequences in Each Class | | Total Number of mRNA Molecules in Each Class |
|---|---|---|---|---|---|
| Abundant class | 12,000 | × | 4 | = | 48,000 |
| Intermediate class | 300 | × | 500 | = | 150,000 |
| Scarce class | 15 | × | 11,000 | = | 165,000 |

One major use is for the assay of the transcriptome (the set of RNAs expressed in a given sample of cells, tissue, or organisms) or portion thereof. The invention can be used to assay specific DNA sequences in chromosomal DNA or in DNA samples cloned and amplified by PCR or by other methods. The nucleic acids detected can be quantified using mass spectrometry in combination with isotopically labeled standards.

Invention methods address many of the drawbacks in currently available methods for assessing gene expression. Invention methods, for example Mass-Spectrometric Analysis of Gene Expression (MAGE) allow a parallel, unambiguous quantification of differentially expressed genes, and would be particularly suited to quantifying those genes that For each target sequence that one wants to detect, one or more oligonucleotides are designed that specifically hybridizes with the target sequence. Oligonucleotides have a tag linked to it, with such tag being removable under appropriate conditions. Two classes of tags are used in the invention: detector tags and selector tags.

As used herein, a detector tag is a chemical moiety that can be detected by mass spectrometry which also provides a means of quantification. Each nucleic acid target sequence is associated with a tag having a specific mass. Peptoids are useful tags because they are compatible with nucleic acid hybridization of the oligonucleotide to which they are attached.

Peptoids, as used herein, are oligomers of N-substituted glycines (or "oligopeptoids," see FIG. 4, and Figliozzi et al., 1996, *Methods Enzymol.* 267:437–47, incorporated by reference herein). Peptoids are well suited for generation of tags and also for creating combinatorial libraries of such tags (see e.g., Linusson et al. (1999) Molecular Diversity 4:103–114). They have a single repeated linking chemistry scheme, a wide variety of monomer substitutions can be chosen, and they are thermally, chemically, and biologically stable. The behavior of peptoids in high-performance liquid chromatograph (HPLC) and capillary electrophoresis has been well studied (see e.g., Robinson et al., J. Chromatography B (1998) 707:247–255; Robinson et al., Journal of Chromatography B, (1998) 705:341–350; Barron. Vreeland, Polymer Preprints (2000) 41:1018–1019; Heerma et al., J. Mass Spectrometry, (1997). 32:697–704; and Wagner et al., *Combinatorial* Chemistry and High Throughput Screening, (1998) 1:143–154) Creation and manipulation of the libraries of peptoid tags via a robotic protocol are relatively easy because the peptoids are synthesized on solid phase supports and have a high yield at each step. Isotopic tags, by used of $^{13}$C-bromoacetic acid or isotopic amine residues, can easily be incorporated into peptoids. Peptoids do not naturally occur and thus "look" distinctly different from peptides and other naturally occurring components of cell lysates and other biological samples.

Figure 5:
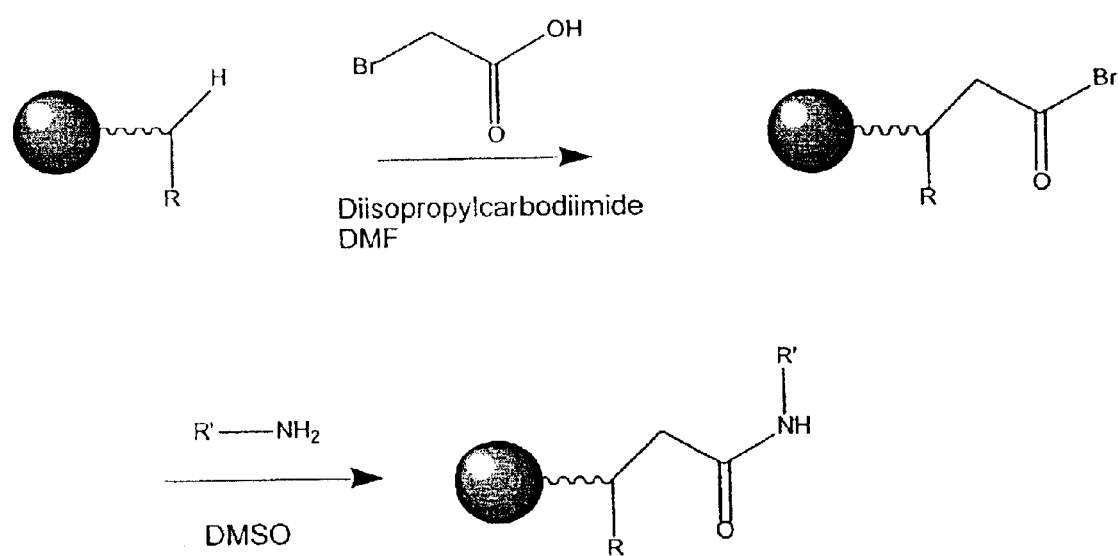
FIG. 5 shows peptoid synthesis via the method of Figliozzi et al. (1996). Variable R or R' represent the variable side chains chosen from among the over one thousand commercially available amines. The first step is an acylation, followed by the second step, a nucleophilic substitution. These steps are alternated until the desired chain is obtained, at which point any groups that require it are deprotected and the oligomer is cleaved from the resin.

Synthesis of peptoids is accomplished by a two-step submonomer reaction cycle using methods known to those of skill in the art (see FIG. 5). An initial acylation step is followed by nucleophilic substitution. These two steps are repeated until a peptoid chain of the desired length is reached. Substituent groups are then deprotected (if protection from synthesis conditions was needed) and the peptoid is cleaved from the resin.

There are over one thousand candidate amines that can be purchased commercially for use in peptoids, but perhaps as few as twenty or thirty highly suitable ones can be used in invention methods. Exemplary amines that can be used in invention methods include benzylamine, methoxyethylamine, propylamine, phenethylamine, glycine, serine, aniline, butylamine, pentylamine, hexylamine, cyclohexylamine, methylcyclohexylamine, bromoaniline, choloroaniline, ethanolamine, furfurylamine, methylamine, ethylamine, 2,2-diphenethylamine, tyramine, ethylcyclohexylamine, methoxypropylamine, butylene diamine (for creating peptoid dendrimers), and the like. Essentially it is desirable that incorporation of one or more amines results in peptoids that are water soluble and do not bind nonspecifically to nucleic acids, e.g., DNA, or other peptoids. The amines should substitute, i.e., be incorporated into the peptoid, with high yield, and the amine-containing products should be bromoacetylated in high yield. It is desirable that the amines included in the peptide have a range of masses and general hydrophobicity so that the resulting peptoids can be separated using a variety of convenient chromatographic methods. The amines should not contain any unprotected functionalities that will interfere with any other chemistry involved in invention methods.

Peptoids can be produced in small numbers using solid phase synthesis vessel methods, or in large numbers in parallel using robotic protocols much like those for peptides and oligonucleotides. They are grown on the same solid supports used for peptides. They can be extended to longer than thirty bases if necessary, in high yield, and are cleaved from the support in a fashion that depends on the support chosen, but often acid or base labile linkers are chosen since they are easily available.

Peptoids can serve as detector tags because they are chemically compatible with the other chemistries required and they are relatively easy to make. Furthermore, the N-substitution, independently chosen on each repeating peptoid unit, allows the construction of a library of peptoids having a rationally determined distribution of one or several properties, such as mass, charge, size, shape, fluorescence, polarity, etc. The peptoids can range in mass from about 300 Da to about 5000 Da. For example, a peptoid constructed using five successive methoxyethylamine submonomer substitutions weighs 592 Da and is quite suitable.

Figure 6:
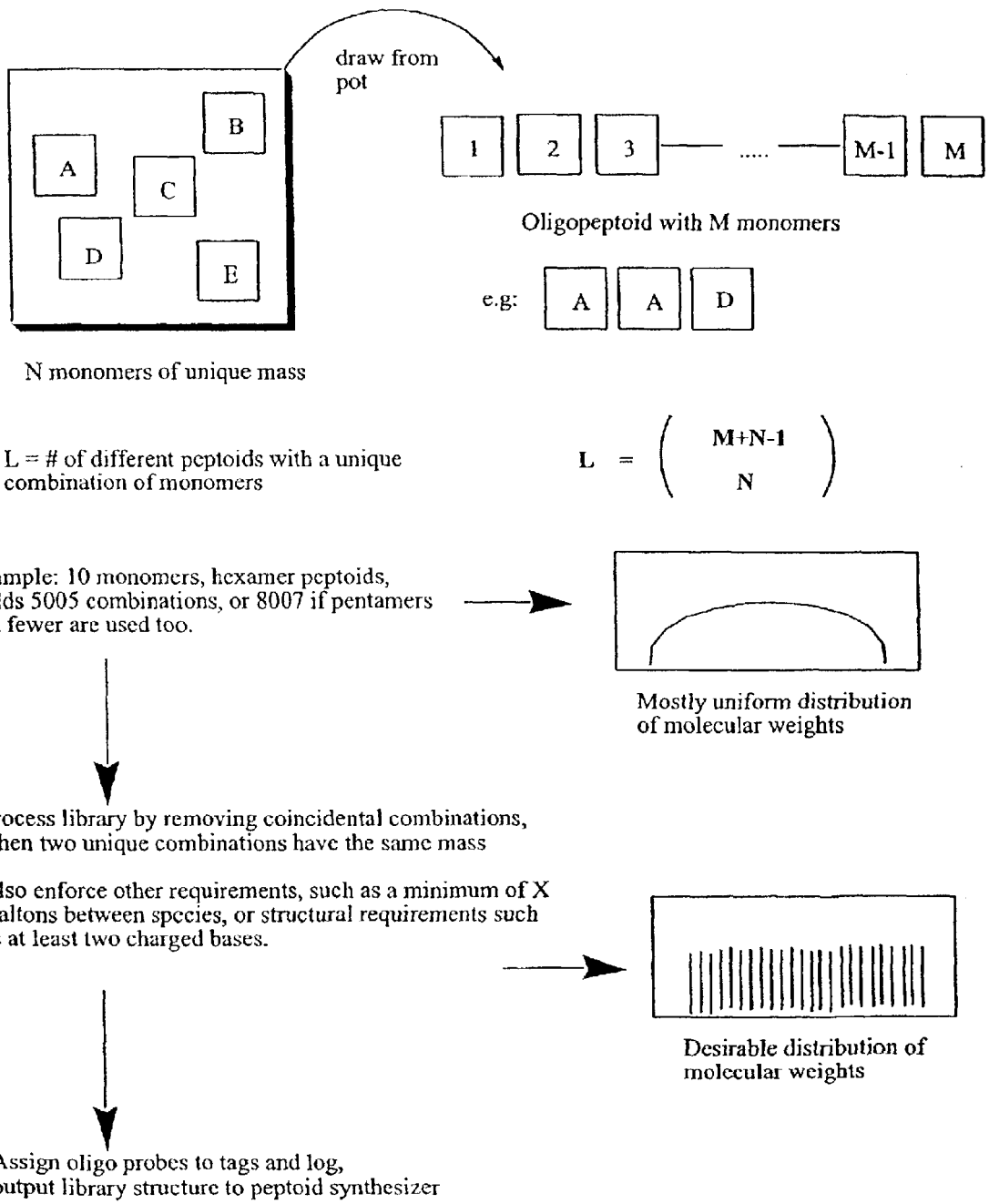
FIG. 6 shows the scheme for synthesizing a rational library of peptoids for use as detector mass tags. An interactive computer program can perform these tasks and assist in designing the most useful libraries.
Figure 7:
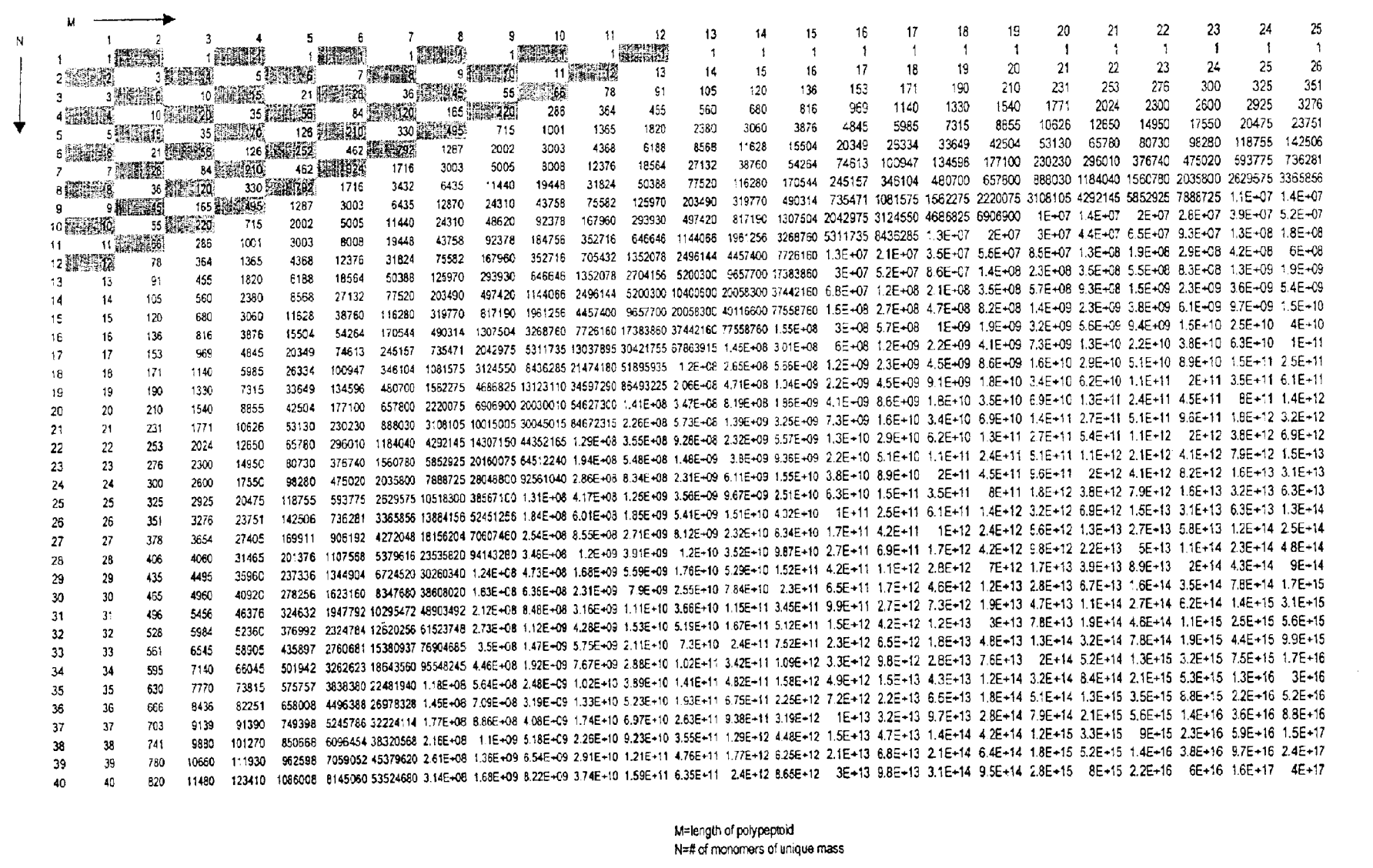
Figure 8A:
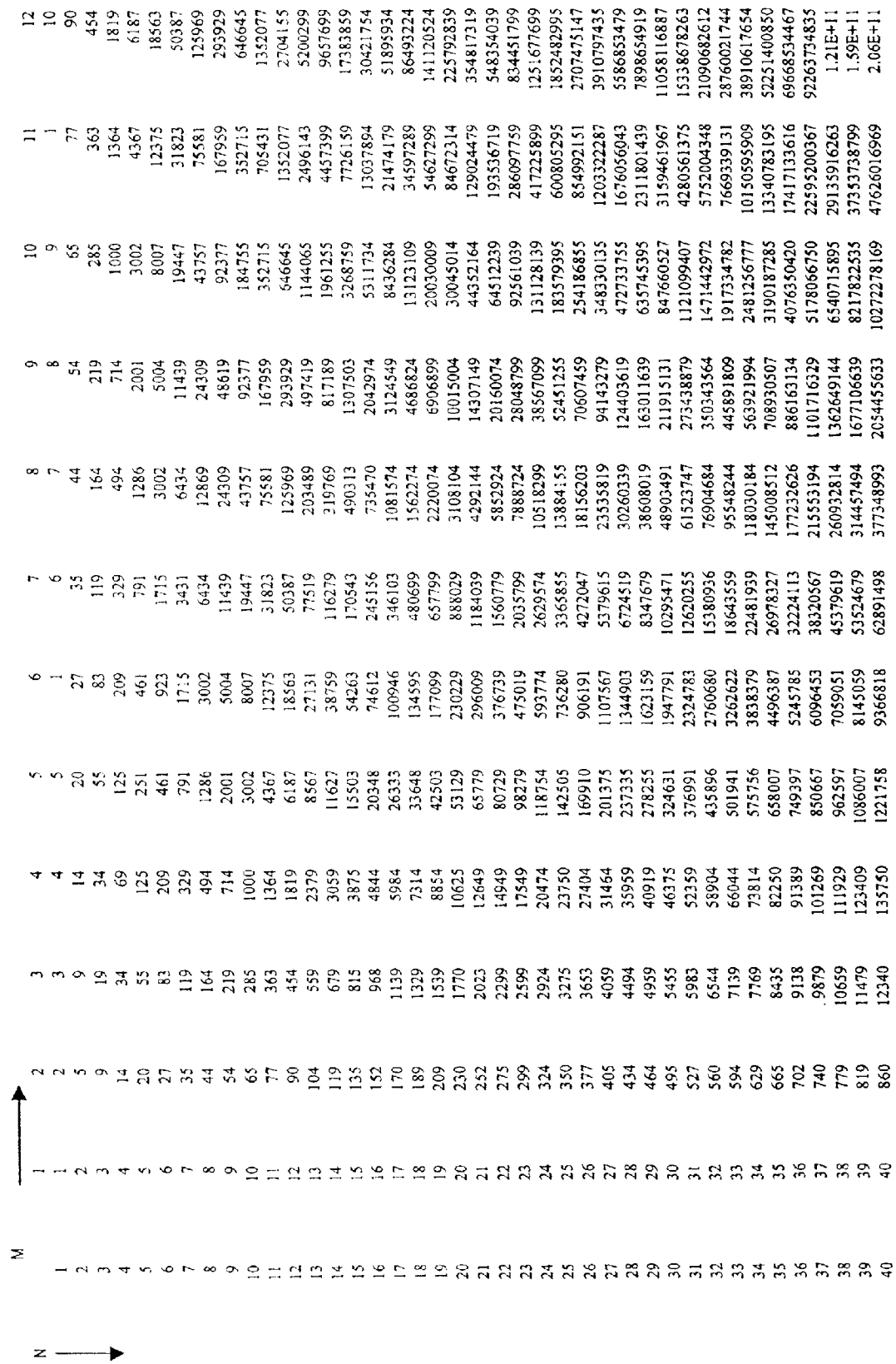
FIGS. 8A and B shows cumulative combinations of peptoids. The variables are the same as in FIG. 7, but for a given M, all peptoids that are shorter than M are also included.

When more than one peptoid detector tag is in a reaction mixture, i.e., when more than one nucleic acid in a sample is detector or when a peptoid library is used, the peptoids should be separated by at least as much mass as each peptoid is separated from its isotopic control, e.g., if peptoid and peptoid isotopic control are separated by 5 Da, then the next peptoid (for the next gene) should be another 5 or so Da heavier. Alternatively, the peptoids could be staggered to fit between each other, assuming that one can compensate for natural isotope abundances. With respect to charge, a negative or neutral charge is desirable. One or more negative charges per amine submonomer can be used. Total charge per peptoid can range from zero to a number depending on the length of the peptoid and choice of amines. When ten amines with a free carboxylic acid each (e.g., glycine) are used, a −10 charge is obtained. This can be determined using a zeta potential machine. A negative charge would not attract DNA, while a positive charge would bind DNA nonspecifically, interfering with the recognition event of hybridization. With respect to size of peptoids, bulky amines like diphenethylamine could restrict folding/bunching of the peptoid while small amines such as ethylamine or propylamine will reduce the peptoid's overall size and might allow more bunching. The relative bulkiness of the molecule would affect its properties in separation techniques that use size such as size exclusion chromatography. Certain particle sizes can be large enough to visualize with scanning electron microscopy. Peptoid oligomers are a variety of three-dimension shapes. They are known to form various structures, some as elaborate as alpha-helices. The degree of hydrophobicity of a peptoid is a critical property. The peptoid will need to be almost completely water soluble. Methoxyethylamine, ethanolamine, glycine, and the like, for example, are more water soluble than benzylamine, proylamine, and the like, and peptoids formed from those amines have similar characteristics. A peptoid trimer of benzylamine submonomers is not water soluble. A peptoid pentamer of two methoxyethylamines, two benzylamines, and a glycine, is water soluble. Additionally, to aid in tracking the peptoids during the method, peptoids can be tagged with a moiety that absorbs or fluoresces, e.g., fluorescein, rhodamine, bodipy™ differently from the sample, e.g., a cell lysate, and other elements involved in invention methods. An example of this rational design is depicted in FIG. 6. Numerical examples follow in FIGS. 7 and 8.

A large number of peptoids of unique masses can be generated using only a small number of primary amines of different masses (Table 2). L oligomers of unique mass (combinations of monomers, not permutations of monomers) are possible given a maximum oligomer length of M and N primary amines of different mass to use as submonomers. The analytical expression that generates the data in Table 2 is a cumulative combination expression:

$$L = \sum_{i=1}^{M} \binom{i+N-1}{N}.$$

A large number of peptoids of unique masses can be generated using only a small number of primary amines of different masses (Table 2). L oligomers of unique mass (combinations of monomers, not permutations of monomers) are possible given a maximum oligomer length of M and N primary amines of different mass to use as submonomers. The analytical expression that generates the data in Table 2 is a cumulative combination expression:

$$L = \sum_{i=1}^{M} \binom{i+N-1}{N}.$$

The generative function for the examples shown does not account for species with identical masses but different structures—these species can be eliminated if the library is created combinatorially, or not created in the first place if the library is created piece-wise. The entire human genome could be encoded with nine-mers formed from only nine different primary amines. Significant clusters of genes could be studied with tetramers formed from four different primary amines. It is probably beneficial to use shorter peptoids to increase mass resolution in the detection phase and increase the oligomer-to-oligomer differences for chromatography.

must cleave in high yield, preferably quantitatively, in a consistent manner. The chemistry used to cleave the linker must not damage the detector tag, for example, a peptoid.

Several general strategies can be to generate an oligonucleotide to a detector tag (see FIG. 9 and Examples 1 to 4). Most start with a solid support such as a resin. Using chemistry known in the art, DNA residues can be attached in a sequential manner followed by attachment of a linker, followed by sequential attachment of peptoid residues. Alternatively, peptide residues can be attached in a sequential manner to the resin, followed by the linker, followed by sequential attachment of DNA residues. In another strategy, a pre-formed peptoid having one or more residues is attached to the resin, followed by attachment of DNA residues connected together, i.e., an oligomer, which has a linker attached. The converse strategy, i.e., attachment of a pre-formed oligomer followed by attachment of a preformed peptoid having a linker attached. When a solid resin support is not used, a pre-formed peptoid containing a linker can be attached to a pre-formed DNA residue. The strategy chosen depends on whether pre-purification of the reaction product is desired, and whether undesirable chemical incompatibilities can be avoided.

Detector oligonucleotides (when the detector tag is a peptoid) can be constructed with a variety of schemes. Since both oligonucleotides and peptoids are synthesized on solid-phase supports, one could synthesize them subsequently (or "on-line"). This requires that either the peptoid be exposed to oligonucleotide synthesis conditions, or that the oligonucleotide be exposed to peptoid synthesis conditions. This

TABLE 2

|       | M = 1 | 2  | 3   | 4   | 5    | 6    | 7     | 8     | 9     |
|-------|-------|----|-----|-----|------|------|-------|-------|-------|
| N = 1 | L = 1 | 2  | 3   | 4   | 5    | 6    | 7     | 8     | 9     |
| 2     | 2     | 5  | 9   | 14  | 20   | 27   | 35    | 44    | 54    |
| 3     | 3     | 9  | 19  | 34  | 55   | 83   | 119   | 164   | 219   |
| 4     | 4     | 14 | 34  | 69  | 125  | 209  | 329   | 494   | 714   |
| 5     | 5     | 20 | 55  | 125 | 251  | 461  | 791   | 1286  | 2001  |
| 6     | 6     | 27 | 83  | 209 | 461  | 923  | 1715  | 3002  | 5004  |
| 7     | 7     | 35 | 119 | 329 | 791  | 1715 | 3431  | 6434  | 11439 |
| 8     | 8     | 44 | 164 | 494 | 1286 | 3002 | 6434  | 12869 | 24309 |
| 9     | 9     | 54 | 219 | 714 | 2001 | 5004 | 11439 | 24309 | 48619 |

A library of peptoids with unique, masses distributed over a wide range, and having properties that are compatible with hybridization conditions, cleavage conditions, and enzymatic steps, e.g., ligation, can be designed. The library can be catalogued so that each unique mass is associated with the oligonucleotide that it tags. Optionally, amines can be incorporated into certain peptoids that give the peptoids a strong and unique signature that can be readily observed with a detection device, to allow easy quantitation of single species, and for the purposes of generating stock solutions. For example, amines that provide peptoids with a strong signal using UV/Visible detection can be used. Peptoids are also very stable to storage on resin or as a lyophilized powder.

The manner in which the peptoid detector tag is linked to the oligonucleotide is crucial for the success of invention methods. The linker must be relatively easy to form and the chemistry used to form it must not damage the tag or the oligonucleotide. The reaction should be highly specific and allow complete purification of the products which reduces the contribution to noise during the quantitation step. Very importantly, the linker must resist breakage during any further oligonucleotide preparation steps, the hybridization step, and any separation steps. When the linker is cleaved, it has been done successfully with peptide-oligonucleotide conjugates, but a considerable amount of adjustment has to be made to standard synthesis procedures, which is not convenient with a shared facility synthesizer (Truffert et al., Tetrahedron Letters, (1994) 35:2353–2356 and de la Torre et al., Tetrahedron Letters, (1994) 35:2733–2736. A further difficulty is adapting peptoid chemistry, which is based on a submonomer scheme that makes use of harsher reagents than that of peptide chemistry, to the on-line synthesis scheme. The most straightforward method for on-line synthesis is to produce the oligonucleotide of interest, add one of several phosphoramidites that contain a cleavable linker, and then terminate the nucleic acid portion of the conjugate with a 5' amine modification. This primary amine could be used to initiate a peptoid synthesis. This process has a low yield and the purine nucleic acids may not successfully withstand the direct acetylations used in peptoid synthesis. Any one-pot scheme that is attempted requires significant modification of either the peptoid synthesis conditions or the oligonucleotide synthesis conditions, and considerable optimization. It also leads to a complex final purification step.

In a two-pot scheme, the oligonucleotides and peptoids are produced via standard protocols, purified and kept for future uses. Oligonucleotide or peptoid, or both, is modified either during their solid-phase syntheses, or afterwards, and they are coupled. The final product mixture is simpler to purify than the result of the one-pot scheme because there is only one representative of each species of oligomer, instead of the normal mixture of partial products produced during solid-phase synthesis.

There are two major options for the linkage chemistry. Either the cleavable moiety is added prior to the conjugation, which is done via a permanent linkage, or the conjugation leads to the formation of a cleavable linker directly. In the latter method, the typical choice would be to form a disulfide linker between the oligomers under oxidizing conditions, which can later be reduced. The disulfide bond is not extremely stable across a variety of conditions, and the most worrisome trait of a cleavable linker would be premature cleavage, because that would result in lost signal. One method for performing a post-synthetic conjugation (FIG. 13) that leads to a disulfide bond is to make use of the heterobifunctional crosslinker SPDP (N-Succinimidyl 3-(2-pyridyldithio)proprionate).

Alternatively, the cleavable moiety could be added prior to conjugation, either to the peptoid or to the oligonucleotide. A commercially available phosphoramidite, the building block for automated DNA synthesis, contains a alkyl chain broken by a disulfide bond. Normally, this is reduced post-synthesis so it can be used as a terminal thiol group. If it were left on, a further phosphoramidite could be added 5' to the disulfide bridge that contains a free amine. The amine could be used for a permanent conjugation to a peptoid. One slightly modified version of this scheme makes use of a commercially available branched phosphoramidite (Juby et al., Tetrahedron Letters (1991) 32:879–882) that has the Fmoc protecting group used for peptide synthesis and the DMTO protecting group used for oligonucleotide synthesis (FIG. 12).

Figure 11A:
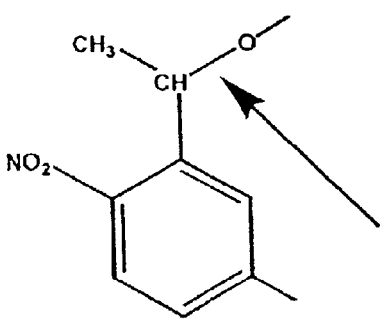
FIG. 11A shows an orthonitrobenzene moiety that can be photocleaved at the location indicated by the arrow by long wave UV light.

Another method for generating a cleavable linker is to make use of recently developed bio-compatible photolabile moieties based on ortho-nitrobenzene (FIG. 11A). No mechanism has been indicated yet, but if a polymer chain either passes through the phenyl ring, or is adjacent to the phenyl ring, and the orthonitro group is neighbor to another bond such as an amide or phosophodiester, then long-wave ultraviolet light can cause the neighboring bond to cleave. The extent of cleavage and the products depend on the configuration of the neighboring groups. Linkers based on ortho-nitrobenzene are used often for solid-phase supports, when the chemistry to be done on the solid phase involves both acidic and basic conditions, so a linker is required that is stable to both acid and base.

Figure 11B:
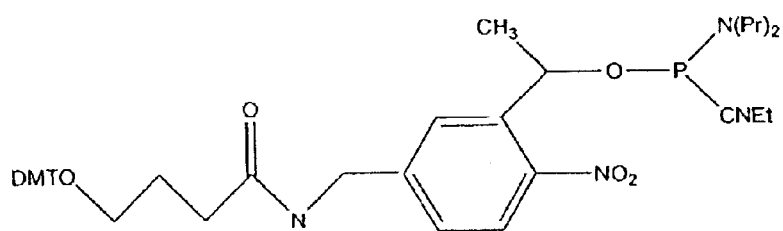
FIG. 11B shows a phosphoramidite for automated synthesis of DNA, available from Glen Research Corp., it that makes use of the orthonitrobenzene moiety to provide a photocleavable link.

The most efficiently cleaving implementation of the ortho-nitrobenzene moiety was developed recently for use in DNA oligonucleotides (Olejnik et al., (1996) Nucleic Acids Research 24:361–366). Optimization of neighboring groups and structures yielded a cleavable linker that is stable to acid and base, and cleaves quantitatively in five minutes upon exposure to long-wave ultraviolet light Olejnik et al., (1999) Nucleic Acids Research 27:4626–4631). This linker has been incorporated into phosphoramidites and is now available commercially. One disadvantage of this linker is that oligonucleotides containing it are difficult to characterize. MALDI is often used for mass spectrometry of oligonucleotides, and since most MALDI systems ionize the sample with an ultraviolet laser, the sample is partially cleaved in the process. This property is used for solid-phase assays involving this linker (Hahner et al., (1999) Biomolecular Engineering 16:127–133). The most appropriate version of this phosphoramidite is commercially available in a photocleavable-spacer version (FIG. 11B); A phosphoramidite for automated synthesis of DNA, available from Glen Research Corp., it that makes use of the orthonitrobenzene moiety to provide a photocleavable link.

Figure 11C:
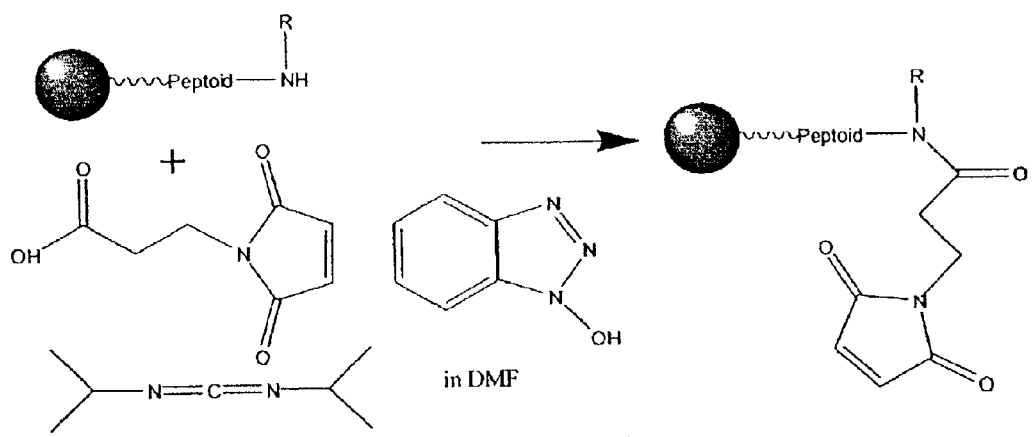
FIG. 11C shows that using 3-Maleimidopropionic acid, a peptoid can be modified to have a terminal maleimido group, which is specifically reactive with thiol groups
Figure 11D:
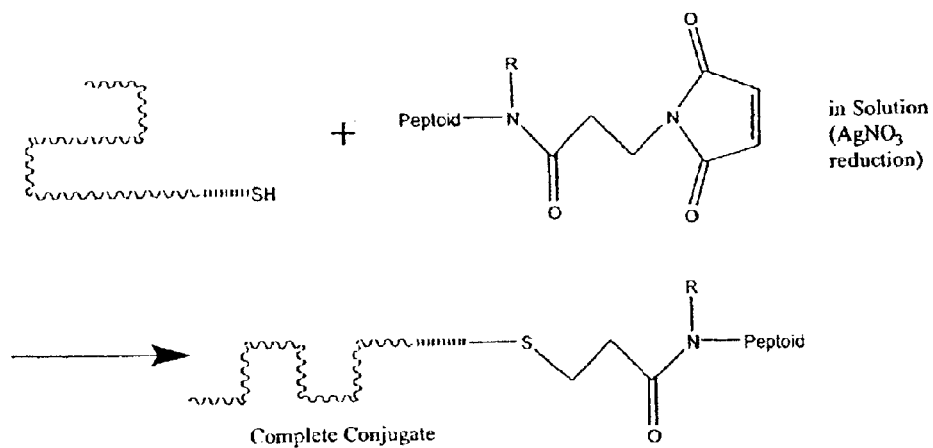
FIG. 11D shows the final steps of conjugation where the peptoid and oligonucleotide are reacted at pH 7.2 in phosphate buffer for 20 hours to form conjugates.
Figure 11E:
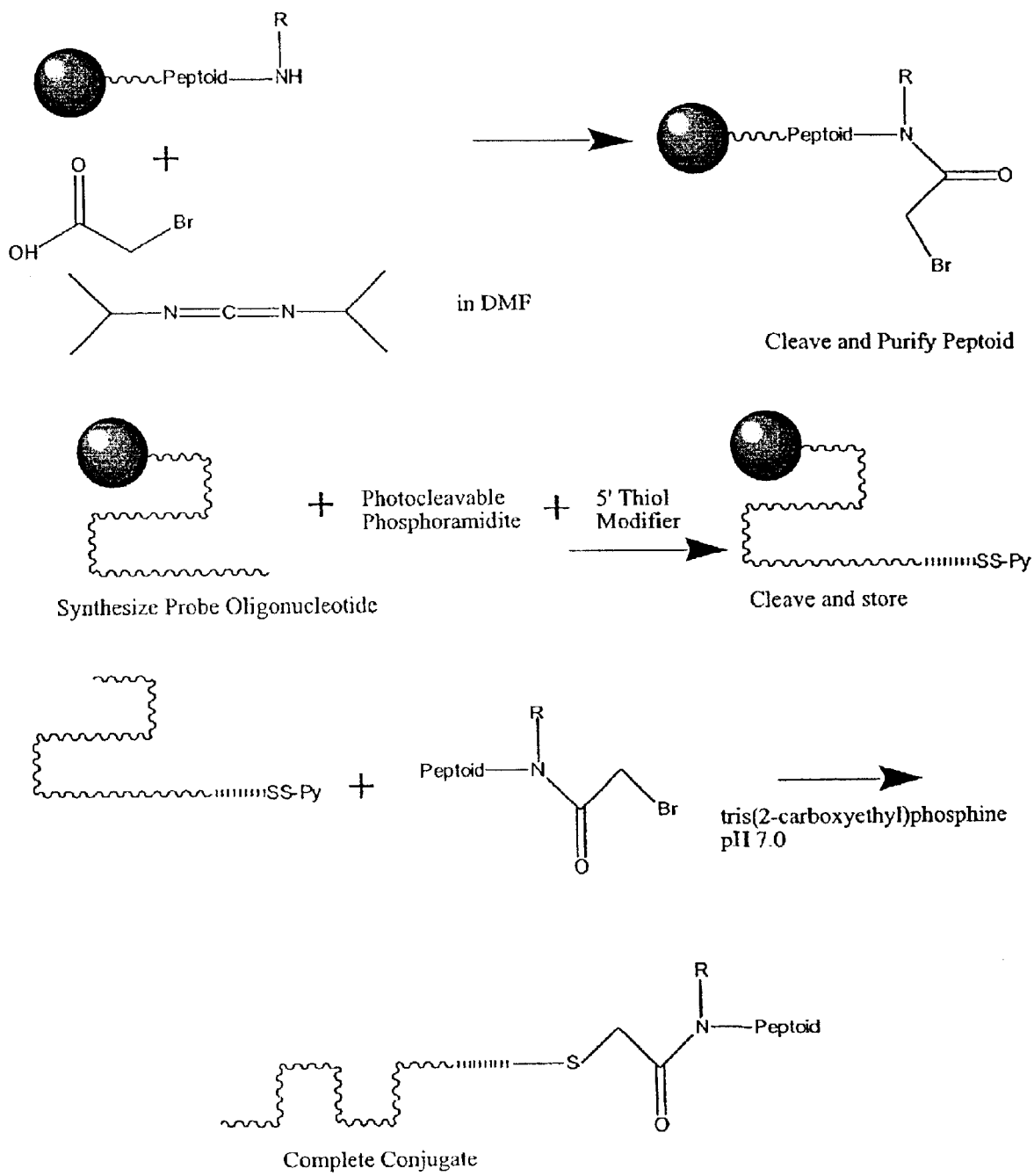
FIG. 11E shows another conjugation scheme that involves making a N-bromoacetyl peptoid, then reacting it with a disulfide oligonucleotide in the presence of TCEP (tris (2-carboxyethyl)phosphine.

Once the cleavable linker is incorporated into the oligonucleotide during the automated synthesis, it is followed by a 5' modifier that will allow the oligonucleotide to be bound to the peptoid. One possibility is to use a 5' amino modifier and continue the synthesis of the peptoid on the same resin. This suffers from the disadvantages of on-line synthesis as discussed herein. Another method would be to use the branched phosphoramidite scheme (FIG. 12) with the photocleavable-spacer instead of the disulfide bridge. This would allow the peptoid to be bound 3' to the oligonucleotide instead of 5'. A common method for post-synthetic conjugation yielding a peptoid 5' to the oligonucleotide is to condense solution phase oligomers to form a thioether bond. The oligonucleotide is synthesized with the cleavable linker, and then terminated with a 5' thiol modification. The peptoid is synthesized separately, and after the final primary amine is substituted, an extra acetylation step is performed using 3-maleimidopropionic acid (FIG. 11C). In the final steps, the peptoid and oligonucleotide are reacted at pH 7.2 in phosphate buffer for 20 hours to form conjugates (FIG. 11D). Another conjugation scheme involves making a N-bromoacetyl peptoid, then reacting it with a disulfide oligonucleotide in the presence of TCEP (tris (2-carboxyethyl)phosphine (FIG. 11E).

Removing the detector tag is performed by subjecting the a moiety having a linked detector tag, for example, a ligated oligonucleotide according to invention methods, to a de-linking agent. A de-linking agent, as used herein, refers to the agent used to cleave the linker that attaches a detector tag to a nucleic acid. The mechanism of the agent, for example, the chemical conditions, must be orthogonal to the other chemical reactions used in the assay. De-linking agents include an acid condition, an alkaline condition, visible light radiation, UV radiation, heat, a reducing condition and an oxidizing condition.

Invention methods include the step of contacting the nucleic acid of interest with at least one oligonucleotide. An oligonucleotide is linked to a selector tag or to a detector tag. Contacting is performed under conditions that allow the oligonucteotides to specifically hybridize with the nucleic acid. Typically, hybridization of mass-tagged detector oligonucleotides with the target nucleic acid population is done under conditions of molar excess of oligonucleotide detectors to target so that little or no desired target remains unhybridized, and under kinetic conditions such that the hybridization is stopped near or beyond kinetic termination. The reaction conditions are also chosen with attention to hybridization stringency so as to favor stable interaction of detector oligonucleotides with their intended target sequences, while at the same time being as unfavorable as is possible for interactions of the detector with non-target RNAs.

As used herein, "specific hybridization" refers to hybridization under low stringency, moderately stringent or highly stringent conditions which distinguishes related from unrelated nucleotide sequences. (See, for example, the techniques described in Maniatis et al., 1989 Molecular Cloning A Laboratory Manual, Cold Spring Harbor Laboratory, N.Y., incorporated herein by reference), In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether target nucleic acids are contacted in solution or rather than immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the Following a hybridization between one or more detector oligonucleotides and a preparation containing potential target nucleic acids, those mass-tagged primers that have hybridized will be separated from the primers that have not hybridized with target nucleic acids. Un-hybridized oligonucleotides can be present because all legitimate targets, that is the nucleic acids of interest, are already hybridized, or because there were no target nucleic acids, i.e., RNAs, complementary to a detector oligonucleotide species. In certain embodiments of the invention, separation is not necessary. In other embodiments, separation can be accomplished by several possible means.

Physical separation of the hybridized detector oligonucleotides from non-hybridized ones (and from other molecules in the reaction mixture) may be accomplished by any of several strategies. These strategies can be designed to be more or less rigorous for eliminating non-hybridized material depending on the signal to noise ratio required during identification of the detector tag. For small input samples, more rigorous separation strategies are usually employed, with a reduction for samples where larger input material is readily available. Contamination with other non-tag material is a second consideration in separation strategies. In a simple form, if the peptoid library is rationally designed, non-expected masses can be discarded. The peptoids that serve as detector tags can also be modified to contain a variety of useful chemical "hooks" or "probes" that would further facilitate easy separation, such as fluorescence, charge, biotin, and the like.

To select hybridized over non-hybridized detector oligonucleotides when the detector oligonucleotide is hybridized to MRNA, one separation method uses the fact that virtually all mRNAs have a poly A tail at their 3' end. Methods for purification on the basis of the presence of poly A are well established. Oligonucleotides having peptoid detector tags are well-suited to this type of separation because the peptoids do not interfere with the separation. Similarly, the presence of 5' cap structures on the RNA can be employed. Using the poly A separation scheme, all mRNAs and detector oligonucleotides that are stably associated with mRNA, would be separated from unhybridized oligonucleotide. The power of the separation can be enhanced (with a resulting increase in purification and downstream increase in signal to noise ratios) by either combining this with another selection method or by performing multiple iterations of this selection.

High-performance liquid chromatography or capillary electrophoresis are both capable of purifying the probe-target duplexes. The addition of other selector moieties can aid in selecting desired hybridization or amplification products. For example, a distribution of fluorine atoms could be incorporated on the peptoids' amine submonomers, and a fluorous HPLC column could be used to retain the peptoid tags while unmodified nucleic acids pass through.

Another separation strategy takes advantage of the selector tag linked to oligonucleotides, i.e., selector oligonucleotides. Various selector oligonucleotides and separation (purification) methods associated with the various selector oligonucleotides can be used in invention methods. Conjugation of a selector oligonucleotide with a physical or molecular tag that can be used to separate the oligonucleotide allows the separation of unhybridized oligonucleotides linked to selector tag and hybridized oligonucleotide linked to selector tag, for example selector oligonucleotide hybridized to target nucleic acids. The selector tag can be used to separate the selector oligonucleotide from a reaction mixture using an agent that binds to the selector tag. For example, a biotinylated selector oligonucleotide can be separated using avidin/strepavidin binding methods. A selector oligonucleotide tagged with digoxygenin can be separated using anti-digoxygenin affinity reagents. An oligonucleotide linked to a magnetic selector tag, for example, paramagnetic beads, can be separated using a magnetic field. Selector tags can be enzymes with selection by enzyme activity (or the converse). The selector tag can be a fluorescent dye or dye impregnated bead that would allow the use of optical sorting, or would serve as a detection device during or following chromatographic separation. The selector tag can have a very prominent chromatographic feature such as charge or size that would allow simple purification using an ion-exchange column or other column. Exemplary selector tags include tags: a fluorescent compound, a luminescent compound, a chemiluminescent compound, a radionuclide, a paramagnetic compound, and biotin.

In some embodiments of the invention, selector tags are the same for all selection primers when a plurality of selector oligonucleotides is used, rather than specific for each target as the detector tags are. In another embodiment, more than one family of selector primer might be used in the same hybridization mix. This would act as an internal standard within each experiment or to generate more than one family of products for later detector tag analysis, i.e., multiplexing. For example, in a simple form, two selector tags can be used with each selector tag used in combination with the same group of detector tags to detect the same group of targets. The hybridized target nucleic acids would be separated from the reaction mixture and into two groups based on the selector tag, and processed independently (removal of the detector tags). Since the selector tag does not interfere with hybridization, each selector tag-selected nucleic acid group should be the same. The two-fold redundancy provides and internal control for method reliability.

In an alternative embodiment, a primer family can be used to increase the multiplexing capacity of the method. For example, when identification by mass spectrophotometric analysis is limited to simultaneously detecting about 20 to 30 peptoids, a family of selector tags, from about 5 to about 10, about 15, or about 20, can be used in combination with a set of detector probes. In other words, the same detector tag can be associated with more than one oligonucleotide probe or primer and each detector tagged oligonucleotide that hybridizes with a unique target polypeptide target sequence will be "binned" with one selector tag from a family of selector tags. This strategy can increase the total multiplexing capability in a reaction mixture by one to two orders of magnitude.

Any affinity scheme that would allow physical isolation of selector oligonucleotides from non-hybridized detector primers as classes of molecules could be used, but the enhancement of specificity is retained only if they are ultimately co-purified due to the fact that a selector primer has become attached to a detector primer because both have annealed to the same RNA or DNA target. The type of selector tag employed depends on cost, yield, ease of manipulation, efficiency and ability to obtain good separations on varied sample quantities. In some applications of invention methods, very small amounts of sample are contemplated.

For both selector and detector classes of oligonucleotide, the particular nucleotide sequences used and the length of those sequences can be optimized for each invention method and for each particular method use. A typical length for oligonucleotides (RNA or cDNA) linked to detectors or selectors ranges from about five to forty nucleotides, but some considerations might make either shorter or longer ones appropriate. In any case, sets of detectors and selectors matched for similar Tm (a measure of melting temperature) when they are to be reacted together in the same mixture (multiplexed) is desirable. Short oligonucleotide sequences are likely to anneal to multiple genes. Short oligonucleotides (e.g., 5 to 10 mers) can be used in order to detect the total quantity of the complementary sequence(s) in the sample, for example, to identify a specific nucleotide motif. A motif may identify a gene family, or one gene function, but may not necessarily identify the gene itself. Long oligonucleotides (about 50 to 70-mers or as long as 100 mers) can be used to ensure as much specificity as possible. This would be helpful when the sample contains a very complex mixture of nucleic acids or when detecting a sequence in a sample that has two or more homologous sequences. When invention methods are used to identify gene expression in a sample, the oligonucleotide length chosen for the primer or probe is as short as necessary to specifically identify each gene Testing of sequence sets to exclude undesirable cross hybridization with each other (both informatic tests and bench tests) can be used to optimize multiplex determinations. It is envisioned that a set of detector oligonucleotides and selector oligonucleotides would eventually be designed to be compatible with each other and to include all genes for a given organism or all gene products. Subsets could then be used at will, as the experimental or clinical case demands. Modified oligonucleotides with alterations in bases, sugar, base modifications or backbone modifications might become desirable to enhance stability or to facilitate later separation from the tags or to improve their shelf-lives.

Following separation using selector tag, the detector tag is removed from the hybridization product. The hybridization product refers to the nucleic acid of interest to which is hybridized an oligonucleotide linked to the detector tag, and, optionally, in certain embodiments, an oligonucleotide linked to a selector tag. Strategies for removal of the detector tag are identified herein. Following its removal from the hybridization product, the detector tag is identified, allowing detection, and optionally, quantification of the nucleic acid of interest.

Invention methods exploit the advantages of mass spectrometry for nucleic acid detection and the measurement of nucleic acid abundance. This is not as straightforward as merely submitting an unknown mixture of nucleic acids to mass spectrometric analysis, because the mass of a transcript alone does not determine its sequence uniquely. Furthermore, the signal strength of an individual component in a mixture does not correspond to its abundance in the mixture since different compounds ionize to different extents in ESI (electrospray ionization) or MALDI (matrix-assisted laser desorption ionization) spectrometry. Mass spectrometry methods can be used to identify oligonucleotides in a mixture (Pomerantz et al., J. Am. Chem. Soc., 19:3861–3867) but for the reasons described above, mass spectrometry can not be directly used to measure the oligonucleotides. An assay that makes use of mass spectrometry for quantification is desirable, however, because mass spectrometer sensitivity has reached the zeptomole region (about 6000 molecules) and below, and dynamic ranges in excess of six orders of magnitude. This level of sensitivity exceeds any available method for reliable single-transcript quantification, much less any multiplexed method, and is invaluable when assessing of scarce transcripts. Thus, an indirect method of quantification using mass spectrometric analysis is used in invention methods.

Figure 16:
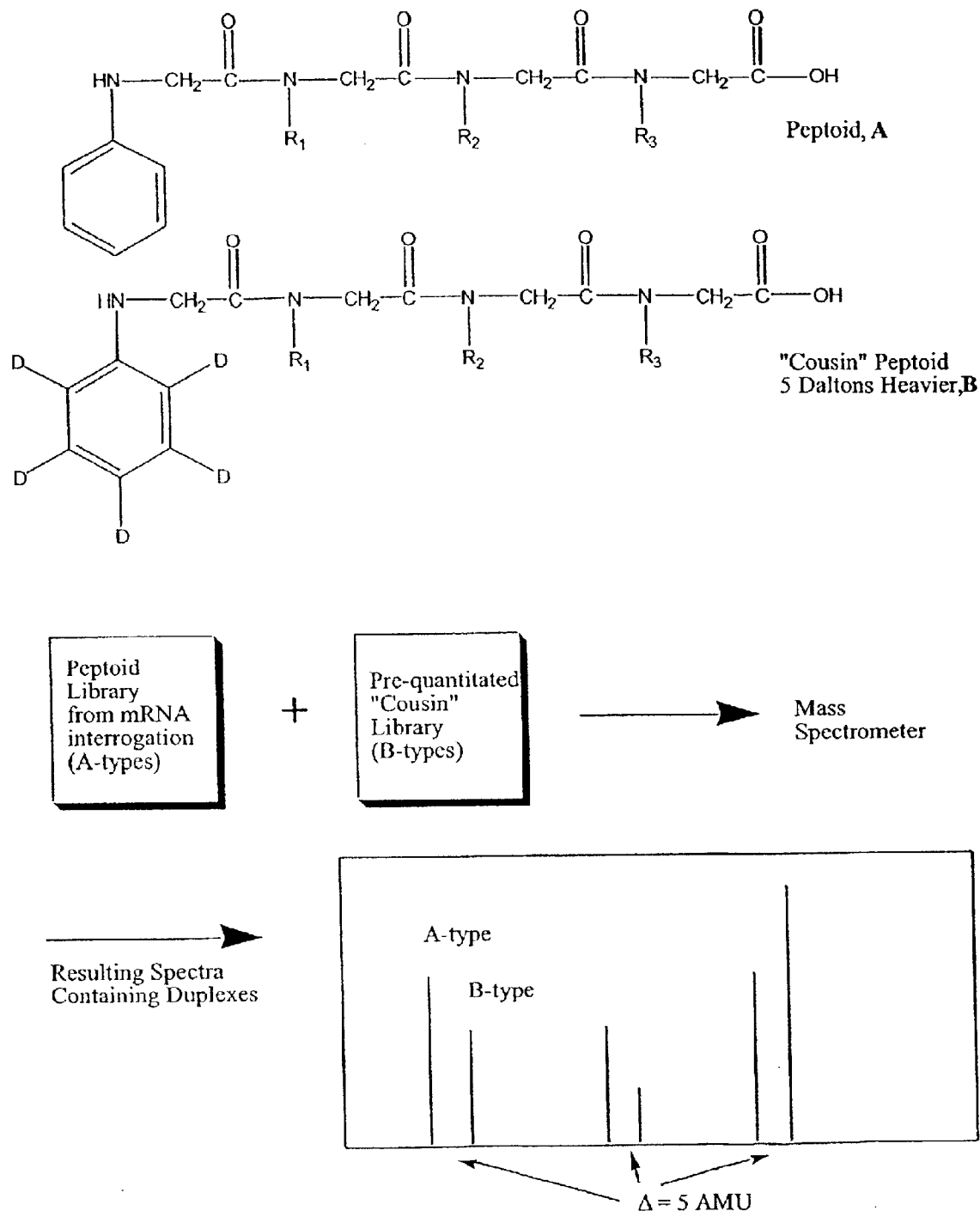
FIG. 16 shows that by mixing a pre-quantitated, cousin library of mass-shifted isotopic peptoids, duplex peaks appear on the spectrograph. The relative height of each peak in a duplex reflects the relative abundance of the two species. This overcomes the problem of deconvoluting complex mixture spectra. Five-fold deuteration of an aniline base is shown. $C^{13}$ bromoacetic acid is another viable strategy.
Figure 18:
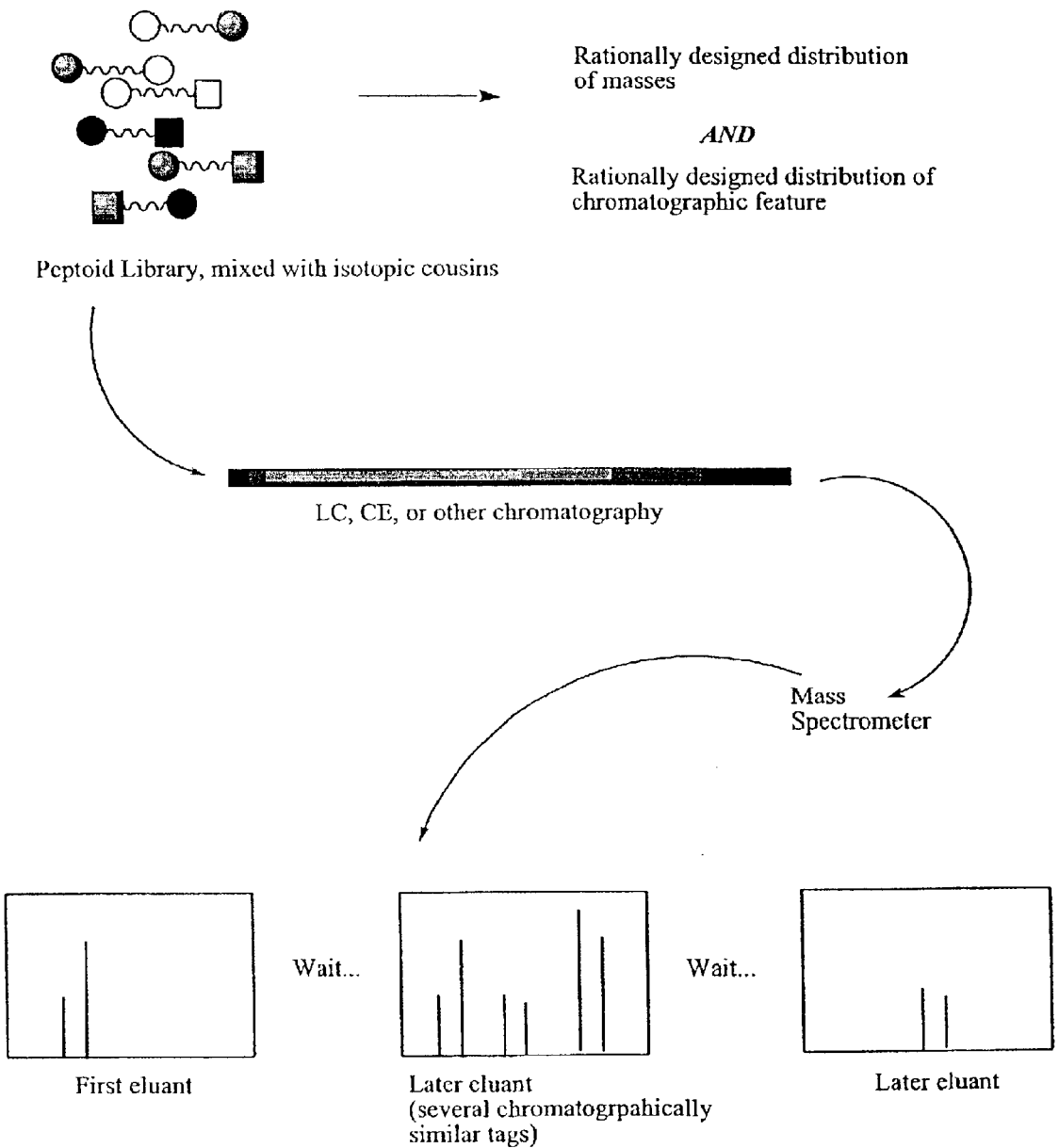
FIG. 18 shows incorporating chromatography with the isotopic scheme for MS detection. This allows fewer duplexes to be read at a time, enhancing the signal-to-noise ratio. Perfect chromatographic separation is not necessary as long as the masses of the tags are unique.

The method of isotopic internal standards will be used to quantify the tags. A scheme based on isotopic labeling can ameliorate complications of quantification due to variations in ionization and other effects (see FIGS. 16 and 17). Each peptoid mass tag will have a chemically identical "cousin" that has been isotopically labeled to be a fixed amount heavier. For example, three carbons of the backbone might be $^{13}$C, or the aromatic ring of a benzylamine side chain could be five-fold deuterated. The particular amount of the shift will depend on the type of mass-spectroscopy and the presence of interfering natural isotopes.

Mass Spectrometric analysis provides high sensitivity and dynamic range (Poulsen et al., Rapid Communications in Mass Spectrometry (2000) 14:44–48; Walk et al., *ESI Fourier Transfer Ion Cyclotron Resonance Mass Spectrometry (ESI-FT-ICR-MS): A Rapid High-Resolution Analytical Method for Combinatorial Compound Libraries.* Angew. Chem. Int. Ed., 1999. 38:1763–1765). The application of mass spectrometry, especially ESI-FTICR (Fourier Transform Ion Cyclotron Resonance) to deconvolution of combinatorial mixtures is a rapidly growing field (Fang et al., Combinatorial Chemistry and High Throughput Screening, (1998) 1:23–33; and Nawrocki et al., Rapid Communications in Mass Spectrometry, (1996) 10:1860–1864; Tutko et al., Rapid Communications in Mass Spectrometry (1998) 12:335–338). ESI is a particularly convenient ionization method, since it is used with chromatographs and is high throughput when compared to MALDI (see Wu and Odom, Analytical Chemistry, (1998): p. 456A–461A). If MALDI is necessary to resolve the peptoids, it will make data interpretation easier if the peptoid masses are not too crowded on the spectra.

Figure 22:
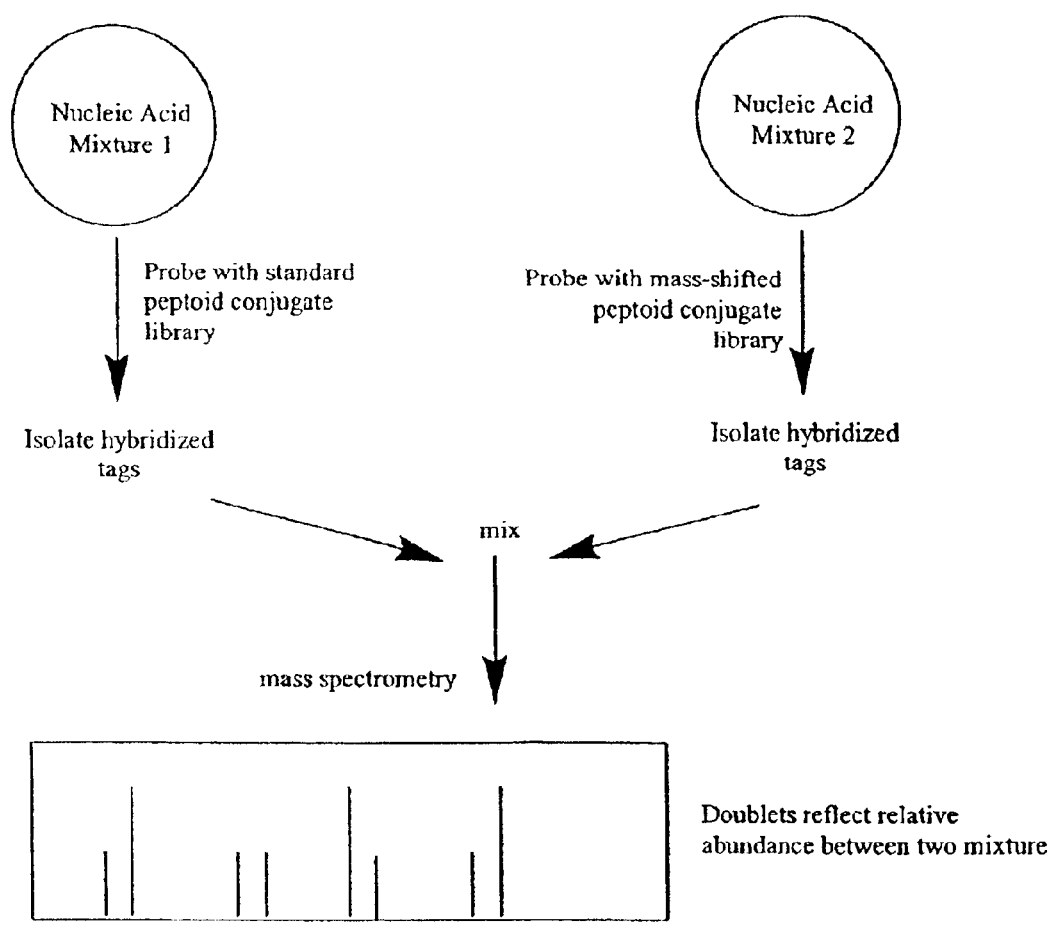
FIG. 22 shows that by using two complete sets of peptoid conjugates, one isotopically shifted from the other, two samples can be interrogated simultaneously, producing comparative data like microarrays.
Figure 23:
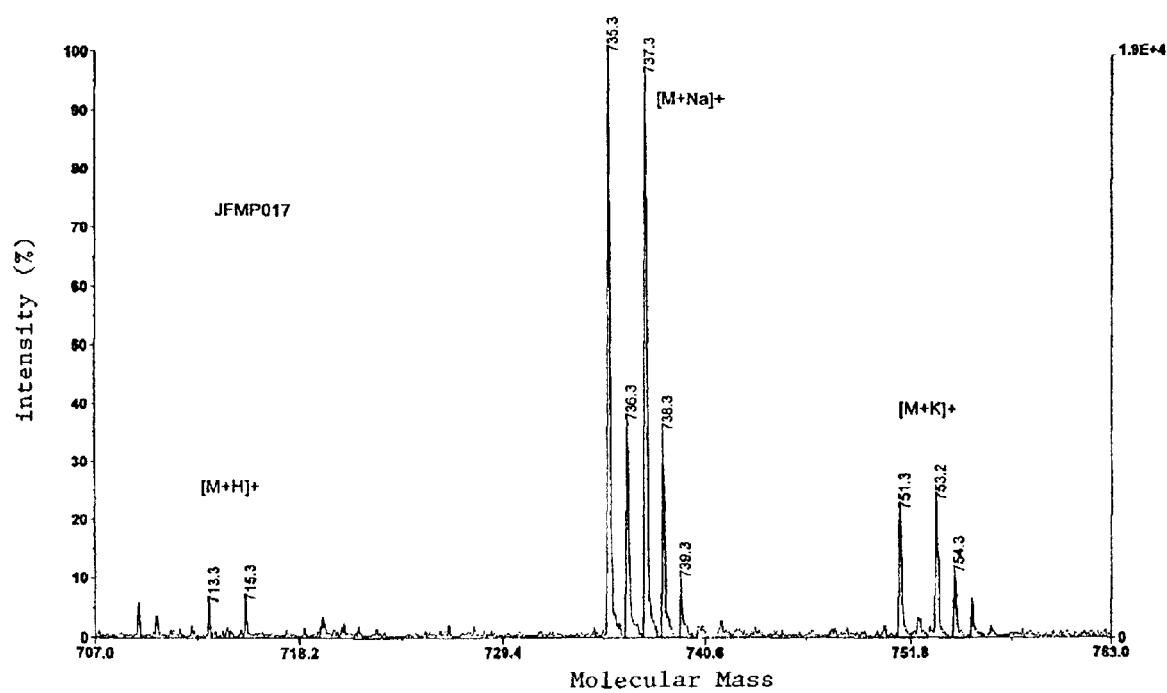
FIG. 23 shows a MALDI TOF spectrum of an n-bromoacetyl peptoid with doublet peaks because bromine is found in nature in two isotopes 2 AMU apart in nearly equal quantity. Thus, not only is the correct mass evidence of the species, but so are the doublet peaks. This is a pentamer of methoxyethylamine with a bromoacetyl tail.

With the right equipment, zeptomole detection is possible, and the dynamic range is beyond six orders-of-magnitude and tunable. For genes that are known to express in very small amounts, small amounts of isotopic standard can be added, so the peaks will be comparable. Similarly, for highly expressed genes, large amounts of standard can be added. Using the cousin peptoids as internal standards could produce exact inventory data on unknown nucleic acid concentrations, much like the SAGE method. However, to eliminate the potential need for carefully standardizing a library of cousins, the entire MAGE assay could be run on two samples (FIG. 22). In the case of gene expression, cells in two different states could be used. One sample would be exposed to the regular peptoid library, the other, to the modified peptoid library. After the peptoid tags are purified, the two resulting mixtures are cotransduced in the mass spectrometer. The relative peak sizes then are a measure of the relative gene expression in the two samples, producing data much like that of DNA microarrays.

Oligonucleotide or nucleic acid sequence refers to a polymeric form of nucleotides. The terms include, for example, a recombinant DNA or which exists as a separate molecule (e.g., a cDNA) independent of other sequences. The nucleotides of the invention can be ribonucleotides, deoxyribonucleotides, or modified forms of either nucleotide. The term polynucleotide(s) generally refers to any polyribonucleotide or polydeoxyribonucleotide, which may be unmodified RNA or DNA or modified RNA or DNA. Thus, for instance, oligonucleotides, as used herein, refers to, among others, single-and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, the oligonucleotides or nucleic acid sequences may contain one or more modified bases. Thus, DNAs or RNAs with backbones modified for stability or for other reasons are "oligonucleotides" as that term is intended herein. Moreover, DNAs or RNAs comprising unusual bases, such as inosine, or modified bases, such as tritylated bases, to name just two examples, are polynucleotides as the term is used herein.

In embodiments of the invention, when a library of peptoids is used as detectors, a second, shifted library is constructed in a known concentration. This library is mixed with the hybridized and purified tags, and serves as an internal standard. With no chromatographic separation, the resulting spectrum will have a large number of peaks, each with a cousin a fixed distance away. The key matter, then, is that because both tags are chemically similar, they will ionize to the same extent. Thus, relative to the internal standard, the amount of the unknown tag can be assayed by comparing the peaks.

Figure 21:
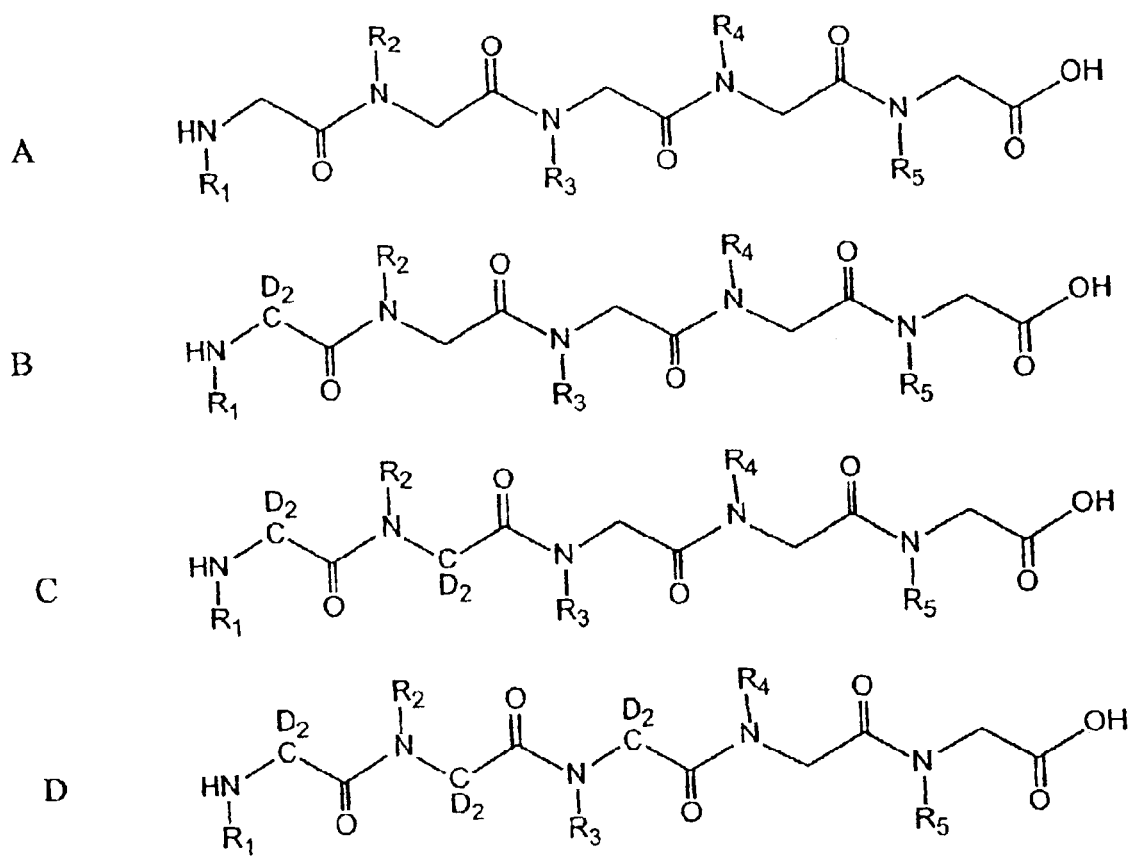
FIG. 21 shows four isotopically shifted peptoids that are chemically identical and each differ by two Daltons. $D_2$-bromoacetic acid was used for one acetylation in oligomer B, two in oligomer C and three in oligomer D.

Additionally, a chromatographic step, such as LC-MS or CE-MS, can be added. This will produce the data one or several peaks at a time, and should increase the signal to noise ratio. Again, because the cousin tags are chemically identical, they will always elute at the same time, and show up on the spectrum as a duplex (FIG. 21).

Another method that might be used is to have a method of cleaving detector from selector tags, and add an isotopic standard selector tag. This could be used for assaying the total amount of mRNA hybridized as a control.

One key area that the use of MS addresses is sensitivity and dynamic range. With the right equipment, single-molecule detection is possible. And the dynamic range is also very great, and tunable. For genes that are known to express in very small amounts, small amounts of isotopic standard are added, so the peaks will be comparable. Similarly, for highly expressed genes, large amounts of standard are added.

The detached tags are analyzed by mass spectrometry, using an internal standards method described later. At the end of this process, the user will deduce whether a particular RNA sequence was present in the original sample (cell lysate, RNA preparation, or other biological sample containing RNA or a nucleotide representation of the RNA such as cDNA) by the presence of the corresponding mass signal from the detector primer (or group of detector primers) that were specific for that mass signal from the detector primer (or group of detector primers) that were specific for that RNA. The presence and absolute or relative amount of a given mass tag will reflect the amount of the target complementary RNA present in the original sample. One can also detect or quantitate sequences corresponding to different parts of a single RNA or cDNA polynucleotide. In general, multiple different oligonucleotides directed at different parts of the same gene will be used as informative internal controls, and (if the same mass tag is used for multiple oligonucleotides directed at the same target) this can also be used to raise sensitivity for a rare target RNA. Other variations on these latter manipulations might also be used in special biological instances to measure the relative concentrations of intron versus exon sequence for a single gene in the sample of the level of 5' end versus more 3' sequences for a particular gene's transcript population.

In another embodiment of the invention, a method is provided for detecting a specific nucleic acid in a sample. The method includes contacting the nucleic acid with a first oligonucleotide linked to a selector tag and a second oligonucleotide linked to a detector tag under conditions that allow the first and second oligonucleotides to specifically hybridize with the nucleic acid such that the first oligonucleotide is located immediately adjacent to the second oligonucleotide, thereby forming adjacently hybridized first and second oligonucleotides.

In this method, the target is cDNA made from the RNA in the sample and the detector primers are DNA or any variation on DNA that can be used by DNA ligase as a substrate. Following hybridization to target cDNA with detector primers and with selector primers, a reaction is performed on the mixture using DNA ligase as the catalyst. Such ligation reactions result in formation of a covalent phosphodiester link between the 3'-most residue of one oligonucleotide and the 5'-most residue of the adjacent annealed oligonucleotide or polynucleotide. The absolute and highly precise requirement for the placement of detector and selector oligonucleotides on the same target cDNA is extremely powerful for improving specificity. For example, if in a single hybridization method, the specificity=X, using this method should improve specificity to a value greater than X squared. Thus the selector and detector oligonucleotides must be precisely adjacent relative to each other and the nucleotides that are joined by ligase must be correctly base paired with the target cDNA. Other embodiments of the invention employ other oligonucleotide species, e.g., RNA, various synthetic analogs, and corresponding ligases, e.g., RNA ligase.

The contacting is carried out in a reaction mixture. Following hybridization, in the reaction mixture, there are the adjacently hybridized first and second oligonucleotides, that is a nucleic acid with the first oligonucleotide specifically hybridized to it and the second oligonucleotide specifically hybridized to it so that the first and second oligonucleotides are immediately adjacently hybridized. Also following hybridization, there are unhybridized first oligonucleotide linked to selector tag, unhybridized second oligonucleotide linked to detector tag, first oligonucleotide hybridized to a nucleic acid without hybridization of second oligonucleotide, and second oligonucleotide hybridized to a nucleic acid without hybridization of first oligonucleotide.

As used herein, "immediately adjacently hybridized" refers to two nucleotides that are complementary to neighboring sites on a nucleic acid so that following hybridization, the 5'-P and the 3'-OH termini of the oligonucleotides can be ligated by the formation of a 5'-3' phosphodiester bond. Ligases such as DNA ligase, for example T4 DNA ligase, and RNA ligase, catalyze the formation of the phosphodiester bond.

Ligation of first and second oligonucleotides forms a ligated oligonucleotide. The ligated oligonucleotide is annealed to the nucleic acid of interest. Such a ligated oligonucleotide bears two tags: one selector tag which was linked to the first oligonucleotide, and one detector tag which was linked to the second oligonucleotide. It is understood that hybridization of the oligonucleotides and ligation of the oligonucleotides does not interfere with the identification of the oligonucleotide.

Identifying the detector tag associated with the ligated oligonucleotide detects the specific nucleic acid in the sample. Identifying the detector tag comprises separating, using the separator tag, the ligated oligonucleotide from the reaction mixture. It is recognized that the selector tag, used as a means to separate the ligated oligonucleotide from the reaction mixture, will also separate from the reaction mixture, un-hybridized oligonucleotide linked to selector tag and non-adjacently hybridized oligonucleotide linked to selector tag. Un hybridized oligonucleotide linked to detector tag and non-adjacently hybridized oligonucleotide linked to detector tag (and remaining components of sample) remain in the reaction mixture.

Using the selector tag to separate the ligated oligonucleotide from the reaction mixture can be accomplished as described herein. Briefly, the selector tag can be contacted with an agent that specifically binds to the selector tag. Identifying the detector tag can be accomplished as described herein.

In another embodiment of the invention there is provided a method for detecting a plurality of specific nucleic acids in a sample. The method comprises contact each specific nucleic acid with an oligonucleotide pair under conditions that allow the oligonucleotide pair to specifically hybridize to the nucleic acid so that the pair members are located immediately adjacent to each other. Each oligonucleotide pair contains an oligonucleotide linked to a selector tag and an oligonucleotide linked to a detector tag. The method includes ligating each adjacently hybridized oligonucleotide to form one more ligated oligonucleotides and identifying the one or more detector tags associated with the ligated oligonucleotides.

A plurality of oligonucleotide pairs is used for detecting a plurality of nucleic acids in a sample. Each oligonucleotide pair contains a first oligonucleotide linked to a selector tag and a second oligonucleotide linked to a detector tag. Libraries of oligonucleotides are provided by invention methods. One such library contains a plurality of first oligonucleotides linked to selector tag. Each oligonucleotide is complementary to a specific nucleic acid or specific nucleic acid target sequence. Such a library can be used to identify a variety of genes, for example to assess gene expression in a sample. The selector tag on each oligonucleotide is not different for each nucleic acid target. The selector tag is chosen because it provides a facile handle for retrieving and physically separating properly hybridized detector oligos through their physical linkage to a companion selector primer. Another library contains a plurality of second oligonucleotides linked to detector tags. Each oligonucleotide is complementary to a specific nucleic acid or specific nucleic acid target sequence. The detector tag on each oligonucleotide is different for each nucleic acid target. A unique detector tag on each detector oligonucleotide allows the identification of the target nucleic acid in a sample. Each library described, i.e., the library of selector oligonucleotides and the library of detector oligonucleotides can be combined to form a library of oligonucleotides in which a selector oligonucleotide can adjacently hybridized to a detector oligonucleotide.

Gains in specificity and in sensitivity come from joining detector and selector oligonucleotides via the polymerase chain reaction. In this embodiment, both detector and selector oligonucleotides act as primers for DNA synthesis, with the product being a DNA duplex containing selector tag on one strand and detector tag on the other, i.e., a "dual-tagged oligonucleotide duplex. The gain in specificity is well understood in the current state of the art to come from the necessity of two simultaneous, high-specificity annealing events that require the sequence content of the target RNA or DNA and its deduced complementary strand.

Accordingly, in another embodiment of the invention, there is provided a method of detecting a nucleic acid in a sample comprising amplifying the nucleic acid with a primer pair to form a dual-tagged amplification product in a reaction mixture, and identifying the detector tag associated with the dual-tagged amplification product. The primer pair is a first oligonucleotide linked to a selector tag and a second oligonucleotide linked to a detector tag.

This embodiment of the invention can significantly increase the sensitivity of the assay by increasing the number of detector tags identified with a single target sequence. Detector and selector tags are both made sufficiently stable to cycling conditions such as thermocycling. Such cycling permits specific amplification of the number of detector tags that will eventually be measured to correspond to a given target sequence. For very small samples or for rare RNA targets, this improves the certainty of detection and can favorably shift the threshold of detection limits.

The invention also contemplates a microfabricated "Lab-on-a-Chip" method. Ideally, gene expression assays would be very fast, and suited for large numbers of samples, as well as accurate. High throughput gene expression assays could be used to study cells in rapid flux, so that better time-dependent maps of gene expression can be constructed. They would also be convenient for diagnostic purposes, allowing medical staff to run these assays without complicated, expensive lab procedures. For instance, gene expression assays are currently being used to diagnose disease, in particular cancer. A rapid diagnostic tool would give physicians the ability to treat conditions with maximal effectiveness.

Figure 20:
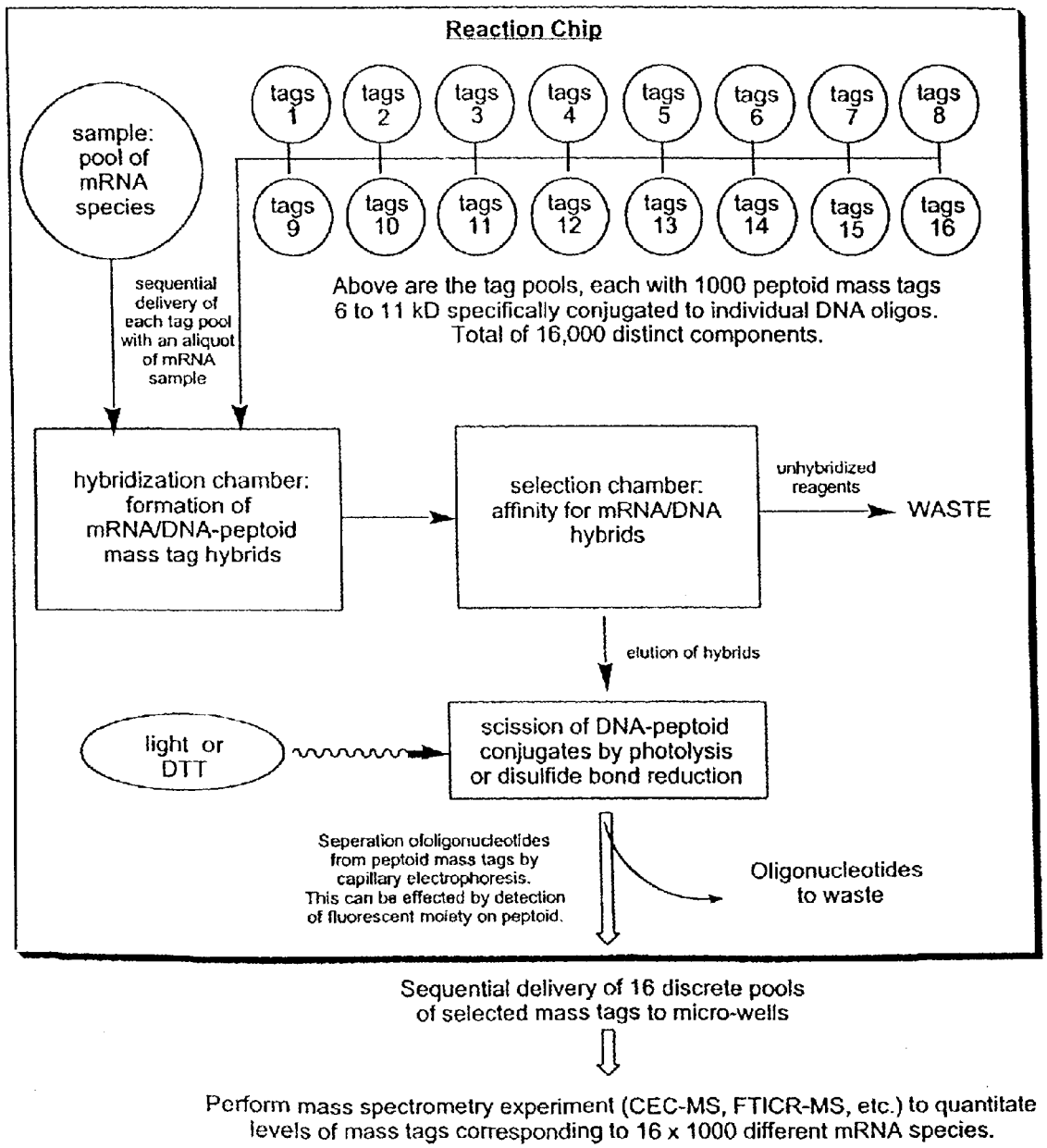
FIG. 20 shows the method for use of MAGE on a microfabricated basis.

Because they involve either sequencing, or hybridization to solid surfaces and subsequent scanning, current methods are not amenable to high-throughput use. In contrast, liquid-chromatography mass-spectrometry (LC-MS) is rapidly becoming an important analytical technique for high throughput combinatorial chemistry, and would be well suited for the analytical portion of mass analysis of gene expression (MAGE). In one manifestation of MAGE, no solid-affinity methods are used, and the entire method could be micronized onto the surface of a chip (see FIG. 20). Wells, pumps, mixing chambers, heating ovens, photo-chambers, CE, and electrospray MS have all been implemented on a chip basis in separate technologies and are known in the art. Designing the peptoid library to allow us to accomplish our separations effectively using CE would eliminate solid-affinity steps. The internal standards are mixed on the chip, and the photo-cleavage is accomplished by shining a laser of the required wavelength onto the chip. The chip would then output the material to the electrospray apparatus of a mass spectrometer. In this example, a complete gene expression assay could be accomplished from isolated mRNA, or more ideally from a cell lysate, in a very short period of time, and the same device could be reused any number of times. The wells that store the mass tags could be programmed to release in a serial fashion, thus allowing the system to multiplex at high speed. In this way, the number of genes that can be assayed could range from one to any number, even as many as the entire human genome contains.

Invention methods can also be used for rapid, large-scale genotyping by constructing a probe conjugate complementary to one version of each single-nucleotide polymorphism (SNP) being studied. The isotopic cousin peptoid would be conjugated to the probe complementary to the other version of each SNP. The ESTs or even genomic DNA (if PNA probes are used) targets are exposed to the probes, and using the protocols described herein, the relative abundance of the polymorphism can be determined. A sample from a single organism should have only one of the two peaks in the doublet, if hybridization conditions are stringent enough, but the doublet that is much larger than the other is likely to be the version of the SNP that is actually present in the sample DNA.

Without further elaboration, it is believed that one skilled in the art can, using the preceding description, utilize the present invention to its fullest extent. The following examples are to be considered illustrative and thus are not limiting of the remainder of the disclosure in any way whatsoever.

EXAMPLE 1

Exemplary oligonucleotides linked to detectors are provided. In a first example, the oligonucleotide is grown on a solid support in a conventional synthesizing robot. Then, the 5' end of the oligonucleotide is modified with two commercially available reagents, which add a disulfide and a free amine. A free amine is the usual starting place for synthesizing a peptoid on an amide resin, so from this point, the resin is transferred to a solid phase synthesis vessel and the peptoid chemistry is executed. Some success was achieved in low yield for a single peptoid base. The result of this kind of linkage is a disulfide, which is easily reduced with DTT. One potential problem is that disulfide bonds may or may not survive the peptoid synthesis and further steps.

Figure 10:
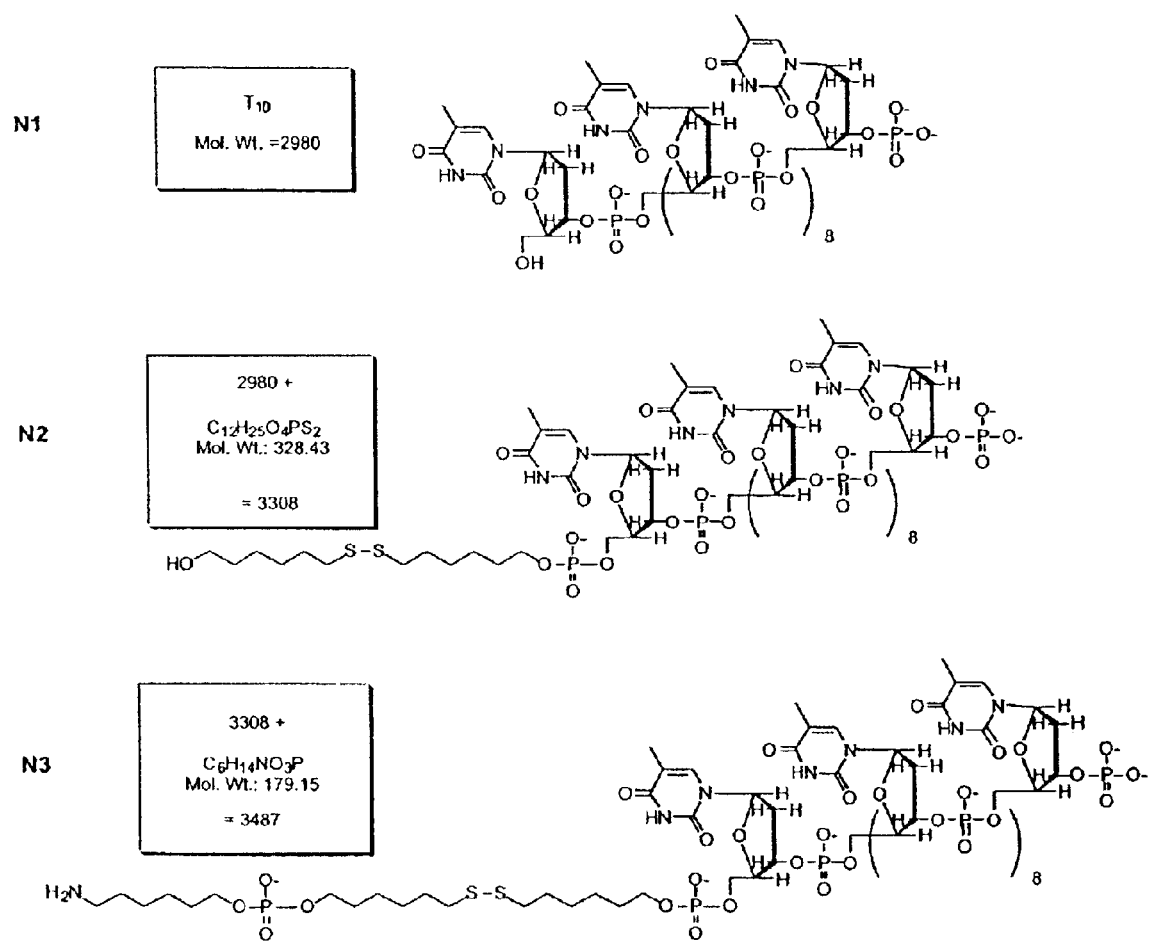
FIG. 10 shows three molecules synthesized on a commercial oligonucleotide synthesizer. N1 is simply dT-10, and then it is modified with a disulfide-containing chain and an amide 5' terminus, both available from Glen Research. MALDI-TOF spectra of these samples are in FIGS. 11a–c. The terminal amine may be used as a site to initiate peptoid synthesis.

In a second example, the peptoid is synthesized first. This avoids exposure of the oligonucleotide to the chemistry of peptoid synthesis. The scheme is depicted in FIG. 10, and it relies on a commercially available phosphoramidite that has a moiety for growing an oligonucleotide as well as an FMOC group for protecting a site for initiating growth of the peptoid. This branched unit could also be combined with the photolabile phosphoramidite.

Figure 13:
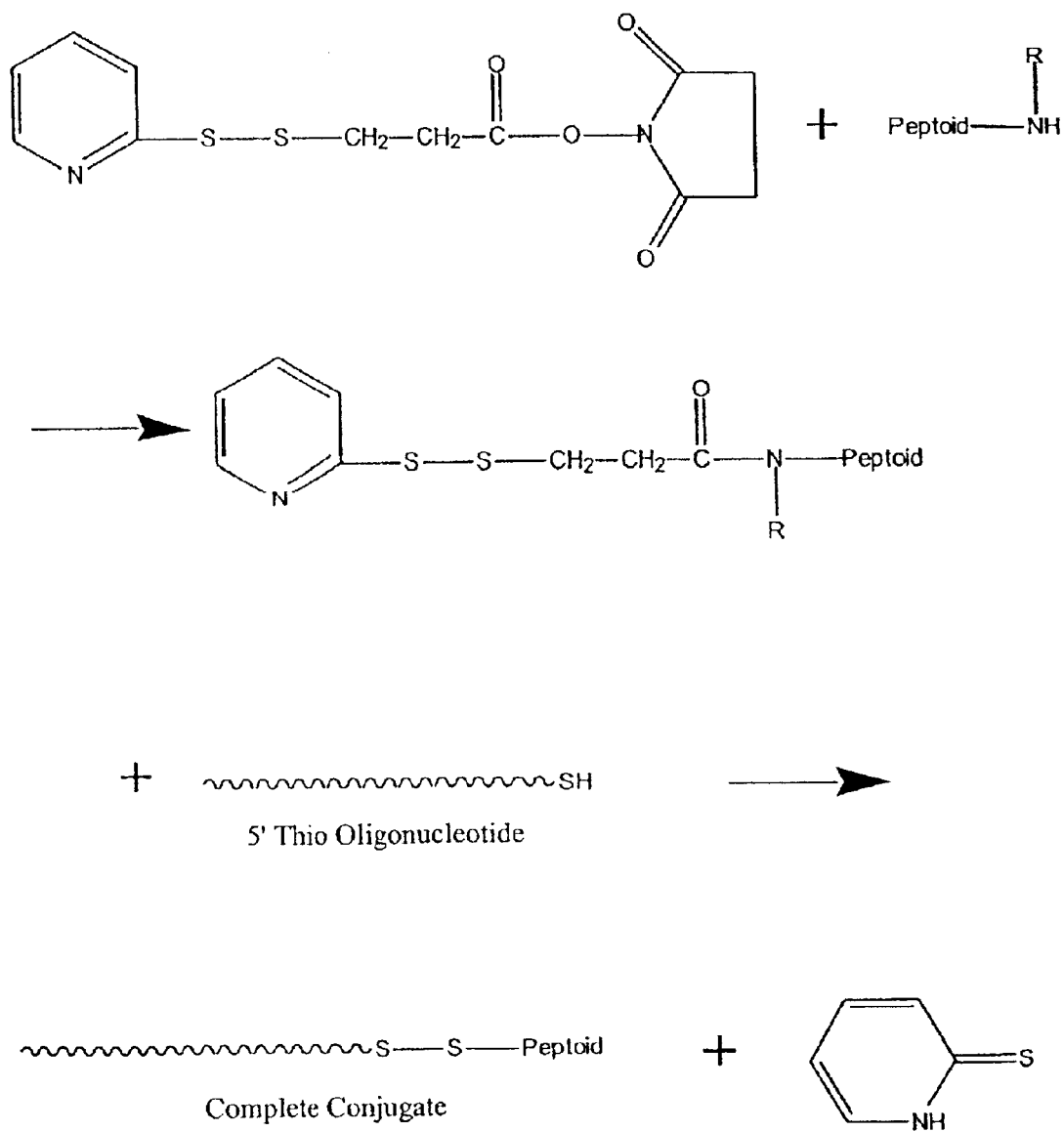
FIG. 13 shows N-Succinimidyl 3-(2-pyridyldithio) proprionate (SPDP) hetero-bifunctional crosslinker (Pierce Chemical) for condensing solution phase oligonucleotides and peptoids with a cleavable, disulfide bond. Literature reports low amounts of undesired cross-products. This scheme could be effected with either the peptoid or oligonucleotide still on support, for ease of separation.
Figure 14:
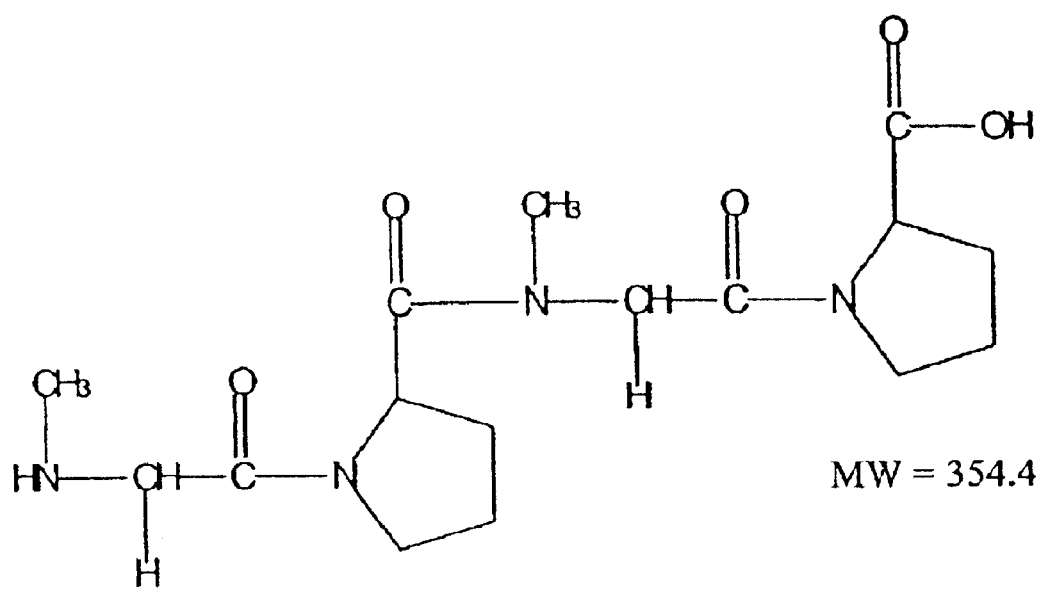
FIG. 14 shows Sarcosine-Proline-Sarcosine-Proline, made on a commercial peptide synthesizer using commercially available FMOC-Sarcosine. In actual implementation, an amide cap was added to the C-terminus.
Figure 15:
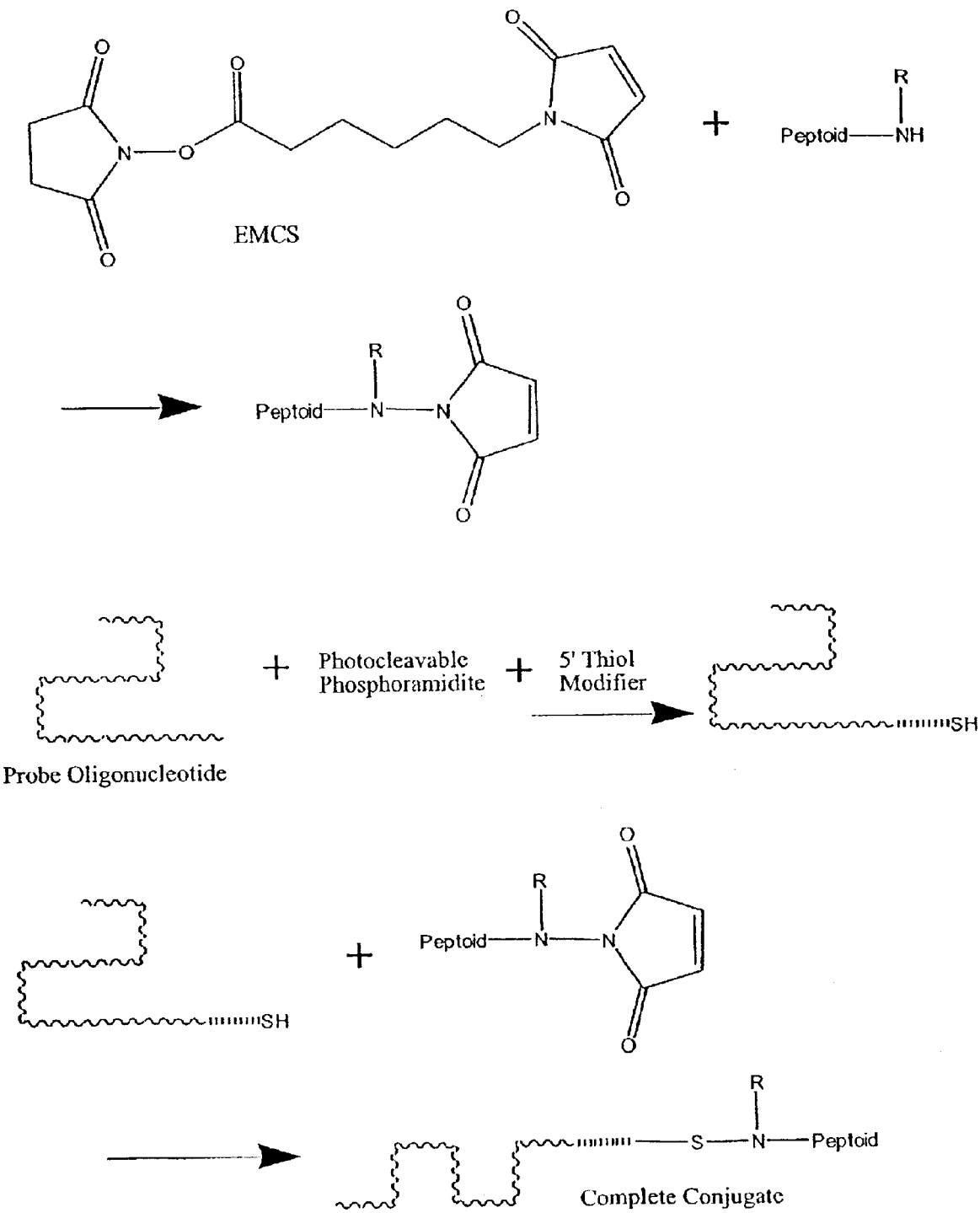
FIG. 15 shows the scheme for creation of thio-ether coupled photocleavable peptoid-ODN conjugate. There are a large number of suitable, commercially available maleimido reagents that could be substituted for EMCS.

In a third example, a complete oligonucleotide and peptoid are first prepared. The peptoid is then reacted with a commercially available protein cross-linking reagent such as SPDP. This scheme is depicted in FIG. 13. An example of a peptoid that could be used for the condensation reaction is "SarProSarPro," depicted in FIG. 14. The end result of this process is the direct condensation of a disulfide. The difficulty of this method is that all of the incomplete products must be purified, using RP-HPLC, or possibly ion-exchange.

In this fourth, preferred example, a phosphoramidite with a photocleavable moiety built in gives a linking function with no additional chemistry. It could be combined with any number of non-cleavable linking schemes between oligonucleotide and peptoid. Many precedents have been established for successfully conjugating peptides to oligonucleotides. One preferred example is to terminate the oligonucleotide in a free thiol, and conjugate the peptoid with a maleimido group. The resulting reaction is extremely efficient and results in a stable thio-ether bond.

EXAMPLE 2

Maleimido-modified Peptoid Synthesis

Peptoid trimers, tetramers and pentamers have been synthesized in high yields manually, using the method of Figliozzi et al, (supra, see also, Table 3). The synthesis described here uses 100 mg of resin, but up to 250 mg have been successfully used in the same size synthesis vessel by scaling up all other reagents linearly. 100 mg of rink amide MBHA resin (Novabiochem, La Jolla, Calif.) is loaded into a 10 mL peptide synthesis vessel that has been modified to improve agitation by adding a small pocket on the wall of the reaction chamber. The resin is first washed several times with N,N-dimethylformamide (DMF, Aldrich Chemical Co., Milwaukee, Wis.). All solvents are purchased anhydrous and kept as dry as possible by careful handling and storage with molecular sieves (3A, EM Industries, Gibbstown, N.J.). The resin is agitated by an upward directed flow of Argon. A wash step refers to adding 1–2 mL of solvent, agitating for 30 seconds, then draining the vessel under aspirator vacuum.

After the initial washing to swell the resin, the DMF is drained and the Fmoc group protecting the resin's free amine is removed by adding 2 mL of 20% piperidine in DMF, agitating for one minute, draining, and adding another 2 mL of 20% piperidine. The second solution is agitated for 15 minutes and then drained. The resin is washed with DMF six times before peptoid synthesis.

At this point, repeated rounds of a single linking chemistry are used. First, the free amine is acetylated by adding 850 μL of 0.6M bromoacetic acid (BAA, Aldrich Chemical Co., Milwaukee, Wis.) and 200 μL of 3.2M diisopropylcarbodiimide (DIC, Aldrich Chemical Co., Milwaukee, Wis.). The slurry is agitated for 30 minutes, drained, and an identical solution is added for a further 30 minutes of agitation. Following this, the mixture is drained, washed twice with DMF, and once with N-methylpyrrohdone (NMP, Aldrich Chemical Co., Milwaukee, Wis.).

The nucleophilic substitution of a primary amine is the second half of a round of synthesis. The primary amine of choice is dissolved at around 1.5 M in NMP and 1 mL of this solution is added to the vessel. The mixture is agitated for two hours, drained, and the resin is subsequently washed twice with NMP and once with DMF. The cycle can be repeated up to 75 times depending on the choice of primary amines. The main source of poor yield is incomplete acetylation due to excess water in the DMF mixtures.

TABLE 3

| Step | Reagent | | Reaction Time | Volume (μL) | Repetitions |
|---|---|---|---|---|---|
| 1 | BAA Addition | 0.6 M bromo-acetic acid in DMF | — | 850 | — |
| 2 | Activation | 3.2 M diisopropyl-carbodiimide in DMF | — | 200 | — |
| 3 | Acetylation | | 30 min | | 2 |
| 4 | Wash | DMF | 30 s | 2000 | 2 |
|   |       | NMP | 30 s | 2000 | 1 |
| 5 | Displacement | 1.5 M primary amine in NMP | 2 h | 1000 | 1 |
| 6 | Wash | NMP | 30 s | 2000 | 2 |
|   |       | DMF | 30 s | 2000 | 1 |

Benzylamine is the most reliable primary amine, and a tetramer synthesized using only benzylamine submonomers had few incomplete products: benzylamine-only containing tetrameric peptoid. Peptoids consisting of benzylamine submonomers only are not water soluble to any appreciable degree, but if methoxyethylamine submonomers are used, water solubility is afforded without a drop in yield. More limited substitution is possible with aniline and forms of substituted aniline like parabromoaniline, parachloroaniline, and orthonitroaniline.

Following the synthesis of an exclusively methoxyethylamine substituted tetramer peptoid, a portion of the resin was removed from the synthesis vessel and the peptoid was cleaved and submitted for analysis. The resulting peptoid was largely free from impurity and was found at the expected molecular weight. The remaining portion of the resin was reserved in the synthesis vessel and subsequently acetylated to attach a pendant maleimido group.

To prepare a maleimido-modified peptoid, approximately 200 mg of rink amide MBHA resin (Novabiochem, La Jolla, Calif.) bearing the desired peptoid, 1600 μL of a 1.2M 3-maleimidopropionic acid (97%, Aldrich Chemical Co., Milwaukee, Wis.), 1.2M N-hydroxybenzotriazole (HOBt, Novabiochem, La Jolla, Calif.) solution in N,N-dimethylformamide (DMF) is added along with an additional 400 μL of 50% v/v 1,3-diisopropylcarbodiimide (DIC, Aldrich Chemical Co., Milwaukee, Wis.) in DMF. This slurry is agitated with a stream of Argon for thirty minutes, drained, and a fresh charge of the same mixture is added and agitated for 30 minutes. The resulting peptoid is worked up in the same way as amine-terminated peptoids. The product is not free from contaminants, and purification using IPLC with a linear gradient acetonitrile in water with 0.1% trifluoroacetic acid over a C4 or C18 column can be used to isolate the desired product.

EXAMPLE 3

Photocleavable Spacer-Modified Olisoonucleotides

In order to test the feasibility of PC-Spacer incorporation (Glen Research, Sterling, Va.), several oligonucleotides were produced by the Caltech biopolymer synthesis facility (Beckman Institute, Caltech, Pasadena, Calif.). Both DNA oligonucleotides contain a stretch of 25 nucleic acids complementary to a gene in Arabadopsis thaliana called APETALA2, and are terminated on their 5' ends by a C6 Thiol modifier (Glen Research, Sterling, Va.). One of the oligonucleotides contains the PC spacer between the coding sequence and the C6 thiol, the other does not. Mass spectrometry agrees with the calculated molecular weights. Both of these are produced in identical yield as determined by measuring the $OD_{260}$ of the product oligonucleotides in DNAse-free water (Gibco, Gaithersburg, Md.). Molecular weights and molar extinction coefficients are listed in Table 4; X is the 5' thiol cap, and Y is the photocleavable spacer. Deconvoluted ESI spectrum of 5'XCTGTTTCCGGCGGCTGAGAACCACC3', FW=8057.5, where X is the 5' thiol modifier, is different from the deconvoluted ESI spectrum of 5'XYCTGTTTCCGGCGGCTGAGAACCACC3', FW=8400.8, where X is the 5' thiol modifier and Y is the PC-spacer.

TABLE 4

| Species | Molecular Weight | Molar Extinction Coefficient (/mM/cm) |
|---|---|---|
| 5'XCTGTTTCCGGCGGCTGAGAACCACC3' | 8057.5 | 254.3 |
| 5'XYCTGTTTCCGGCGGCTGAGAACCACC3' | 8400.8 | 250.3 |

Hydrogenation of 2-(1-cyclohexenyl)ethylamine In order to produce two chemically identical peptoid libraries that are isotopically shifted, the primary amine 2-(1-cyclohexenyl)ethylamine is to be both hydrogenated and deuterated to produce a tool for shifting the molecular weight of two otherwise identical peptoids by two Daltons; Saturation of 2-(1-cyclohexenyl)ethylamine with either hydrogen or deuterium provides isotopically labeled primary amines for peptoid synthesis). Furthermore, multiple substitutions of the saturated product can be used to generate shifts of two, four, six, etc., for "multicolor" applications. Although the olefin primary amine is available commercially (Aldrich Chemical Co., Milwaukee, Wis.), the saturated products are not.

Approximately 300 mg of 2-(1-cyclohexenyl)ethylamine is dissolved in 10 mL of dichloromethane (EM Industries, Gibbstown, N.J.) along with an additional 300 mg of Palladium on activated carbon (10% by weight, Aldrich Chemical Co., Milwaukee, Wis.). This mixture is stirred and occasionally sparged by hydrogen gas under atmospheric pressure. After three hours, an aliquot of the mixture is filtered over Celite (EM Industries, Gibbstown, N.J.). The solvent is removed under vacuum and replaced with deuterated benzene (Cambridge Isotopes, Andover, Mass.) and taken for solution-phase nuclear magnetic resonance (NMR). Results suggest that this mild treatment is able to eliminate the signature of vinyl hydrogens, and that pressurized hydrogenation or more elaborate catalysts will not be necessary.

EXAMPLE 5

On-line Disulfide-based Synthesis

The first method undertaken to join a peptoid to a DNA oligonucleotide was an on-line, DNA first method. First, DNA oligonucleotides were synthesized. These consisted only of thymine residues, because they do not require protecting groups and are likely to be more robust to a straightforward peptoid synthesis. Poly-$dT_{10}$ was produced by the Caltech synthesis facility, and delivered directly without work-up. The 5' end of the oligomer was successively modified with a disulfide containing phosphoramidite and a 5' amine terminator. The polymer beads were removed from the robotic synthesis cartridge and loaded into the peptoid synthesis vessel. A standard round of peptoid synthesis was run to attach a single benzylamine residue to a bromoacetylated DNA oligonucleotide. This led to a very low yield of the desired product and a large quantity of difficult to identify side products as indicated by MALDI-TOF mass spectrometry (results not shown).

EXAMPLE 6

Photocleavable Peptoid Before attempting to make use of the PC-spacer phosphoramidite, the same orthonitrobenzene moiety was incorporated into a peptoid to determine if it is capable of cleaving the neighboring amide bond when photoactivated. Incorporation of the orthonitroaniline submonomer was poor, and the resulting product did not seem to degrade extensively when exposed to longwave UV light.

Conjugate Synthesis As soon as the methyoxyethylamine substituted peptoid tetramers with the maleimido modification have been purified, they can be conjugated to the DNA oligonucleotides with 5' thiol modifications according to the method of Barton and Vreeland ((2000) Polymer Preprints 41:1018–1019. The oligonucleotides are delivered from the synthesis facility with a trityl group blocking the thiol. In order to provide the reducing conditions that will discourage DNA dimerization and remove the trityl group, 12.8 nmol of oligonucleotide is dissolved in 30 μL of 1×triethylammonium acetate buffer (Calbiochem, La Jolla, Calif.) and 4.33 μL of 1M silver nitrate (Calbiochem, La Jolla, Calif.) and incubated for 30 minutes. To this, 5.78 mL of 1M dithiothreitol (DTT, or Cleland's Reagent, Calbiochem, La Jolla, Calif.) is added, and the liquid phase is aspirated and retained. The precipitate Ag-DTT is washed several times, and the supernatant liquids are combined and filtered using Centri-Spin 20 columns (Princeton Separations, Princeton, N.J.) to remove buffer salts. This eluent is then frozen and lyophilized immediately to prevent dimerization. The maleimido-modified peptoid is prepared at a concentration of 12.8 mM in 0.1M sodium phosphate and 0.15 M NaCl buffer at pH=7.2. Ten mL of the peptoid solution is then added to the lyophilized DNA prepared previously, and incubated for 20 h at room temperature. The product of this reaction will be analyzed by both ESI and MALDI mass spectrometry to determine its efficiency. A fraction of the resulting probe will then be exposed to long-wave ultraviolet light for five minutes, and the analysis repeated to estimate the efficiency of cleavage. In order to produce larger numbers of these tags, the assistance of a research group at Northwestern University led by Annelise Barron that has developed a robotic synthesizer for peptoids may be sought.

Isotopic Tag Production After the hydrogenation of 2-(1-cyclohexenyl)ethylamine is repeated on a larger scale to produce several grams of the hydrogenated product, cyclohexylethylamine, the efficiency of its incorporation into peptoids can be tested. This is expected to be high, since primary amines of similar structure such as cyclohexylamine are reportedly substituted efficiently. At the same time, the saturation reaction will be repeated but with deuterium gas instead of hydrogen gas. There is no reason to expect that this reaction would work as well as it does with hydrogen. Once the tags have been produced in sufficient quantity, they can be incorporated into two chemically identical peptoids with different molecular weights. These peptoids will be made into stock solutions of known concentration, and serial dilutions will be performed of mixtures of the two solutions to test the dynamic range, sensitivity, accuracy, and reproducibility of the isotopic tag method using shared facility ESI, MALDI, and available LC-MS devices.

EXAMPLE 6

Hybridization Efficacy

In order to show method efficacy, control oligonucleotides or cloned plasmids of known concentration can be assayed for in the presence of distractor, control nucleic acids. The method for MAGE will be followed and a single nucleic acid target will be the target. The purpose of this experiment will be to determine the level of background noise, and estimate the accuracy of the assay when it is assembled as a whole. The separation method used to eliminate unhybridized probes will most likely be a poly-T resin. Following this, probes will be cleaved and the mixture will be immediately submitted for mass spectrometric analysis without further separation. The peptoid tags will be considerably smaller than the nucleic acids, and its mass is known, so the rest of the spectra can be ignored. The isotopically shifted version of the peptoid tag being used will be added as an internal standard to determine the abundance of the peptoid mass tag, and thus the target nucleic acid. Once this first experiment is complete, the version of MAGE that makes use of the selector tags will be implemented to try to boost the signal-to-noise ratio of the data generated.

EXAMPLE 7

Sensitivity Serial dilutions of either a control nucleic acid in a mixture or purified mRNA from cell culture will be subjected to the MAGE assay. By doing this, the lower limit of the MAGE assay, at least with the mass spectrometers we have easily available, will be determined. More importantly, the reliability of the data as a function of sample size can be determined.

Direct Probing of Cell Lysate Three identical MAGE experiments will be run, on two aliquots from the same cell culture. All will seek to measure the abundance of a particular gene transcript, but one will make use of purified mRNA, one total RNA, and the final, cell lysate. The signal quality and reproducibility will be compared to determine if MAGE can accept unprocessed cell lysate as starting material for measuring gene expression.

Three or More Simultaneous Conditions Chemically identical peptoid tags will be produced at three or more molecular weights using multiple substitutions of the isotopically labeled cyclohexylethylamine. The abundance of a single gene will be measured in as many samples as there are peptoid tags of different mass but identical structure. This would, for instance, greatly reduce the work that goes into measuring a timecourse of gene expression using standard methods like RNase protection assays or real-time PCR. The results could be validated with these methods, and also by running the experiment on standardized solutions of known plasmids instead of unknown RNA from cell culture.

High Frequency Gene Expression Monitoring If MAGE has low material requirements and is fairly high throughput as is expected, the frequency of measuring gene expression during an experiment can be increased significantly without prohibitively expensive reagent use. The abundance of a particular transcript could be measured every minute for an hour after some stimulus, using an easily grown model organism like E. coli. This would demonstrate the potential for MAGE to generate high frequency, high fidelity data invaluable to gene regulation modelers.

Multiplexing All of the above experiments can be conducted on a single or a small group of transcripts, the probes for which could be produced manually if necessary. However, it will be important to consider the extent to which MAGE can be multiplexed. If a robotic method for peptoid synthesis can be harnessed, either combinatorially or rationally, 50 to 100 probe tags using only high suitable primary amine submonomers could be produced and made into stock solutions for later conjugation with DNA oligonucleotides. This is enough probes to study interesting gene clusters in systems of interest, and experiments at this level of multiplexing would demonstrate that MAGE is capable of generating data in amounts useful to biological modelers.

While the invention has been described in detail with reference to certain preferred embodiments thereof, it will be understood that modifications and variations are within the spirit and scope of that which is described and claimed.

What is claimed is:

1. A method of detecting a specific nucleic acid in a sample comprising:

(a) contacting the nucleic acid with a first oligonucleotide linked to a selector tag and a second oligonucleotide linked to a peptoid detector tag, in a reaction mixture under conditions that allow the first and second oligonucleotides to specifically hybridize with the nucleic acid such that the first oligonucleotide is located immediately adjacent to the second oligonucleotide, thereby forming adjacently hybridized first and second oligonucleotides;

(b) ligating the adjacently hybridized first and second oligonucleotides to form a ligated oligonucleotide;

(c) de-linking the detector tag from the ligated oligonucleotide; and (d) identifying the de-linked detector tag, thereby detecting a specific nucleic acid in a sample.

2. The method of claim 1, wherein identifying the de-linked detector tag further comprises separating, using the selector tag, the ligated oligonucleotide from the reaction mixture.

3. The method of claim 2, wherein using the selector tag comprises contacting the selector tag with an agent that specifically binds to the selector tag.

4. The method of claim 2, wherein de-linking the detector tag is performed by subjecting the ligated oligonucleotide to a de-linking agent selected from the group consisting of an acid condition, an alkaline condition, a visible light radiation, a UV radiation, heat, a reducing condition and an oxidizing condition.

5. The method of claim 1, wherein identifying the de-linked detector tag comprises using mass spectrometry.

6. The method of claim 5, further comprising using chromatography.

7. The method of claim 1, wherein the selector tag is a fluorescent moiety.

8. A method of detecting a plurality of specific nucleic acids in a sample comprising:

(a) contacting each specific nucleic acid with an oligonucleotide pair in a reaction mixture under conditions that allow the oligonucleotide pair to specifically hybridize to the nucleic acid such that the oligonucleotide pair members are located immediately adjacent to each other thereby forming an adjacently hybridized oligonucleotides pair, wherein each oligonucleotides pair comprises a first oligonucleotide linked to a selector tag and a second oligonucleotide linked to a peptoid detector tag;

(b) ligating each adjacently hybridized oligonucleotide pair to form one or more ligated oligonucleotides;

(c) de-linking the detector tag from the one or more ligated oligonucleotides; and (d) identifying one or more de-linked detector tags.

9. The method of claim 8, wherein identifying the linked detector tags further comprises separating, using the selector tag, the ligated oligonucleotide from the reaction mixture.

10. The method of claim 9 wherein using the selector tag comprises contacting the selector tag with an agent that specifically binds to the selector tag.

11. The method of claim 9 wherein de-linking the detector tags is performed by subjecting the ligated oligonucleotide to a de-linking agent selected from the group consisting of an acid condition, an alkaline condition, a visible light radiation, a UV radiation, heat, a reducing condition and an oxidizing condition.

12. The method of claim 8, wherein identifying the linked detector tag comprises using mass spectrometry.

13. The method of claim 12 further comprising using chromatography.

14. The method of claim 8, wherein the selector tag is a fluorescent moiety.

15. The method of claim 8, wherein each first oligonucleotide linked to selector tag has an identical selector tag.

16. The method of claim 8, wherein each first oligonucleotide linked to selector tag has a different tag.

17. The method of claim 8, wherein each second oligonucleotide linked to detector tag has a different tag.

18. A method of detecting a nucleic acid in a sample comprising:

(a) amplifying the nucleic acid with a primer pair to form a dual-tagged amplification product in a reaction mixture, wherein the primer pair is a first oligonucleotide linked to a selector tag and a second oligonucleotide linked to a peptoid detector tag;

(b) de-linking the detector tag from the ligated oligonucleotide; and (c) identifying the de-linked detector tag, thereby detecting the nucleic acid in a sample.

19. The method of claim 18, wherein identifying the detector tag further comprises separating, using the selector tag, the amplification product from the reaction mixture prior to identifying the detector tag associated with the amplification product.

20. The method of claim 19, wherein using the selector tag comprises contacting the selector tag with an agent that specifically binds to the selector tag.

21. The method of claim 18, further comprising removing the detector tag from the amplification product prior to step (b).

22. The method of claim 18, wherein de-linking the detector tag is performed by subjecting the ligated oligonucleotide to a de-linking agent selected from the group consisting of an acid condition, an alkaline condition, a visible light radiation, a UV radiation, heat, a reducing condition and an oxidizing condition.

23. The method of claim 18, wherein the selector tag is a fluorescent moiety.

24. The method of claim 18, wherein identifying the detector tag comprises using mass spectrometry.

25. A method of detecting a nucleic acid in a sample comprising:
   (a) contacting the nucleic acid with an oligonucleotide linked to a peptoid detector tag under conditions that allow the oligonucleotide to specifically hybridize to the nucleic acid to form a mixture of hybridized oligonucleotide and unhybridized oligonucleotide;
   (b) separating the hybridized oligonucleotide from the unhybridized oligonucleotide;
   (c) de-linking the detector tag from the hybridized oligonucleotide; and
   (d) identifying the de-linked detector tag, thereby detecting the nucleic acid.

26. The method of claim 25, wherein separating comprises contacting the mixture with an agent that binds to a polyA tail.

27. The method of claim 25, wherein separating comprises contacting the mixture with an agent that binds to a 5'-capped nucleic acid.

28. A method of generating a double-tagged oligonucleotide duplex comprising:
   (a) contacting a single-stranded nucleic acid with a first oligonucleotide linked to a selector tag and a second oligonucleotide removably linked to a peptoid detector tag, under conditions that allow the first and second oligonucleotide to specifically hybridize to the nucleic acid such that the first oligonucleotide is located immediately adjacent to the second oligonucleotide thereby forming an adjacently hybridized oligonucleotide;
   (b) ligating the first and second oligonucleotides thereby forming a duplex having detector and selector tags.

29. The method of claim 28, wherein the selector tag and the detector tag are a peptoid and wherein the selector tag and detector tag are different.

30. The method of claim 1, wherein the method further comprises identifying an isotopic internal standard along with the de-linked detector tag.

31. The method of claim 30, wherein the method further comprises quantitating the relative amount of the de-linked detector tag relative to the isotopic internal standard.

32. The method of claim 17, wherein the method further comprises identifying a corresponding isotopic internal standard for each de-linked detector tag.

33. The method of claim 32, wherein the method further comprises quantitating the relative amount of each type of de-linked detector tag relative to its corresponding isotopic internal standard.

* * * * *

SEQUENCE LISTING

<160> NUMBER OF SEQ ID NOS: 7

<210> SEQ ID NO 1
<211> LENGTH: 31
<212> TYPE: RNA
<213> ORGANISM: Artificial sequence
<220> FEATURE:
<223> OTHER INFORMATION: Detector oligonucleotide

<400> SEQUENCE: 1
caugguagua guacgguacc gucuacggua a                              31

<210> SEQ ID NO 2
<211> LENGTH: 17
<212> TYPE: DNA
<213> ORGANISM: Artificial sequence
<220> FEATURE:
<223> OTHER INFORMATION: Target sequence

<400> SEQUENCE: 2
catcatgcca tggctga                                              17

<210> SEQ ID NO 3
<211> LENGTH: 30
<212> TYPE: RNA
<213> ORGANISM: Artificial sequence
<220> FEATURE:
<223> OTHER INFORMATION: Detector oligonucleotide

<400> SEQUENCE: 3
uagcuuacac cuagggaccu auuucaggcu                                30

<210> SEQ ID NO 4
<211> LENGTH: 17
<212> TYPE: DNA
<213> ORGANISM: Artificial sequence
<220> FEATURE:
<223> OTHER INFORMATION: Target sequence

<400> SEQUENCE: 4
gtggatccct ggataaa                                              17

<210> SEQ ID NO 5
<211> LENGTH: 16
<212> TYPE: DNA
<213> ORGANISM: Artificial sequence
<220> FEATURE:
<223> OTHER INFORMATION: Detector oligonucleotide

<400> SEQUENCE: 5
acgaccggga ttatgg                                               16

<210> SEQ ID NO 6
<211> LENGTH: 26
<212> TYPE: DNA
<213> ORGANISM: Arabidopsis thaliana
<220> FEATURE:
<221> NAME/KEY: misc_feature
<222> LOCATION: (1)..(1)
<223> OTHER INFORMATION: n is the 5' thiol modifier

<400> SEQUENCE: 6
nctgtttccg gcggctgaga accacc                                    26

```
-continued

<210> SEQ ID NO 7
<211> LENGTH: 27
<212> TYPE: DNA
<213> ORGANISM: Arabidopsis thaliana
<220> FEATURE:
<221> NAME/KEY: misc_feature
<222> LOCATION: (1)..(1)
<223> OTHER INFORMATION: n is the 5' thiol modifier
<221> NAME/KEY: misc_feature
<222> LOCATION: (2)..(2)
<223> OTHER INFORMATION: n is the PC-spacer

<400> SEQUENCE: 7
nnctgtttcc ggcggctgag aaccacc                                          27
```